United States Patent
Steinman et al.

(10) Patent No.: US 9,610,326 B2
(45) Date of Patent: Apr. 4, 2017

(54) AMYLOID BETA PEPTIDES AS THERAPY FOR MULTIPLE SCLEROSIS

(71) Applicant: The Board of Trustees of the Leland Stanford Junior University, Palo Alto, CA (US)

(72) Inventors: Lawrence Steinman, Stanford, CA (US); Jacqueline Grant, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/351,858

(22) PCT Filed: Oct. 17, 2012

(86) PCT No.: PCT/US2012/060617
§ 371 (c)(1),
(2) Date: Apr. 14, 2014

(87) PCT Pub. No.: WO2013/059322
PCT Pub. Date: Apr. 25, 2013

(65) Prior Publication Data
US 2015/0157690 A1 Jun. 11, 2015

Related U.S. Application Data

(60) Provisional application No. 61/548,133, filed on Oct. 17, 2011.

(51) Int. Cl.
*A61K 38/17* (2006.01)
*A61K 45/06* (2006.01)

(52) U.S. Cl.
CPC .......... *A61K 38/1716* (2013.01); *A61K 45/06* (2013.01)

(58) Field of Classification Search
CPC ..... A61K 38/00; A61K 38/1716; A61K 45/06
See application file for complete search history.

(56) References Cited

U.S. PATENT DOCUMENTS

| | | | |
|---|---|---|---|
| 2007/0166311 A1* | 7/2007 | Greferath | A61K 39/3955 424/146.1 |
| 2010/0284909 A1 | 11/2010 | Wisniewski et al. | |
| 2010/0291122 A1* | 11/2010 | Matsuda | A61K 31/711 424/185.1 |
| 2011/0002949 A1 | 1/2011 | Savage et al. | |
| 2011/0052611 A1 | 3/2011 | Garsky et al. | |
| 2011/0060035 A1 | 3/2011 | Wisniewski et al. | |
| 2011/0076323 A1* | 3/2011 | Monsonego et al. | 424/450 |
| 2011/0178024 A1 | 7/2011 | Monsonego | |
| 2011/0200531 A1 | 8/2011 | Tan | |
| 2011/0206706 A1 | 8/2011 | Eisenbach-Schwartz et al. | |

FOREIGN PATENT DOCUMENTS

WO WO2012082237 A1 6/2012

OTHER PUBLICATIONS

Mitew et al. Focal demyelination in Alzheimer's disease and transgenic mouse models. Acta Neuropathol. May 2010;119(5):567-77.*
Jones. Neurological disorders: Two sides to β-amyloid. Nat Rev Neurosci. Oct. 2012;13(10):666. Epub Aug. 22, 2012.*
Block et al., "Microglia and inflammation-mediated neurodegeneration: multiple triggers with a common mechanism", Prog Neurobiol (2005), 76(2):77-98.
Dal Bianco et al., "Multiple sclerosis and Alzheimer's disease", Ann Neurol (2008), 63(2):174-83.
Frank-Cannon et al., "Does neuroinflammation fan the flame in neurodegenerative diseases", Mol Neurodegener (2009), 4:47.
Head et al., "A two-year study with fibrillar beta-amyloid (Abeta) immunization in aged canines: effects on cognitive function and brain Abeta", J Neurosci (2008), 28(14):3555-66.
Jellinger, "Basic mechanisms of neurodegeneration: a critical update", J Cell Mol Med (2010), 14(3):457-87.
Lassmann, "Mechanisms of neurodegeneration shared between multiple sclerosis and Alzheimer's disease", J Neural Transm (2011), 118(5):747-52.
Nemirovsky et al., "Amyloid beta-HSP60 peptide conjugate vaccine treats a mouse model of Alzheimer's disease", Vaccine (2011), 29(23):4043-50.
Salminen et al., "Inflammation in Alzheimer's disease: amyloid-beta oligomers trigger innate immunity defence via pattern recognition receptors", Prog Neurobiol (2009), 87(3):181-94.
Steinman, "Inverse vaccination, the opposite of Jenner's concept, for therapy of autoimmunity", J Intern Med (2010), 267(5):441-51.

* cited by examiner

Primary Examiner — Gregory S Emch
(74) Attorney, Agent, or Firm — Pamela J. Sherwood; Bozicevic, Field & Francis LLP

(57) ABSTRACT

The invention provides methods for treating inflammatory diseases by administering to the subject an effective amount of an amyloid beta peptide, where the dose is effective to suppress or prevent initiation, progression, or relapses of disease, including the progression of established disease.

3 Claims, 14 Drawing Sheets

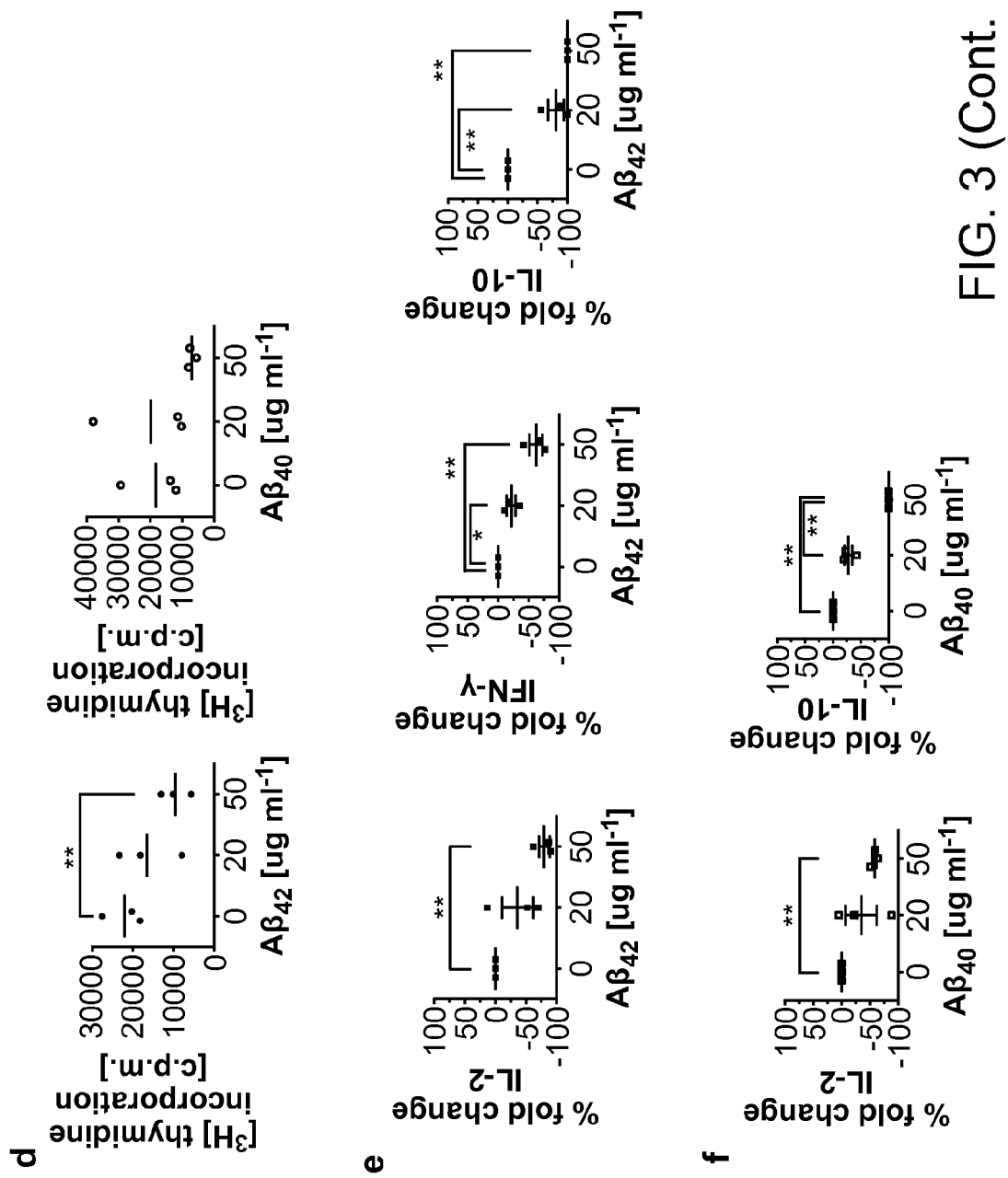
FIG. 3 (Cont. 1)

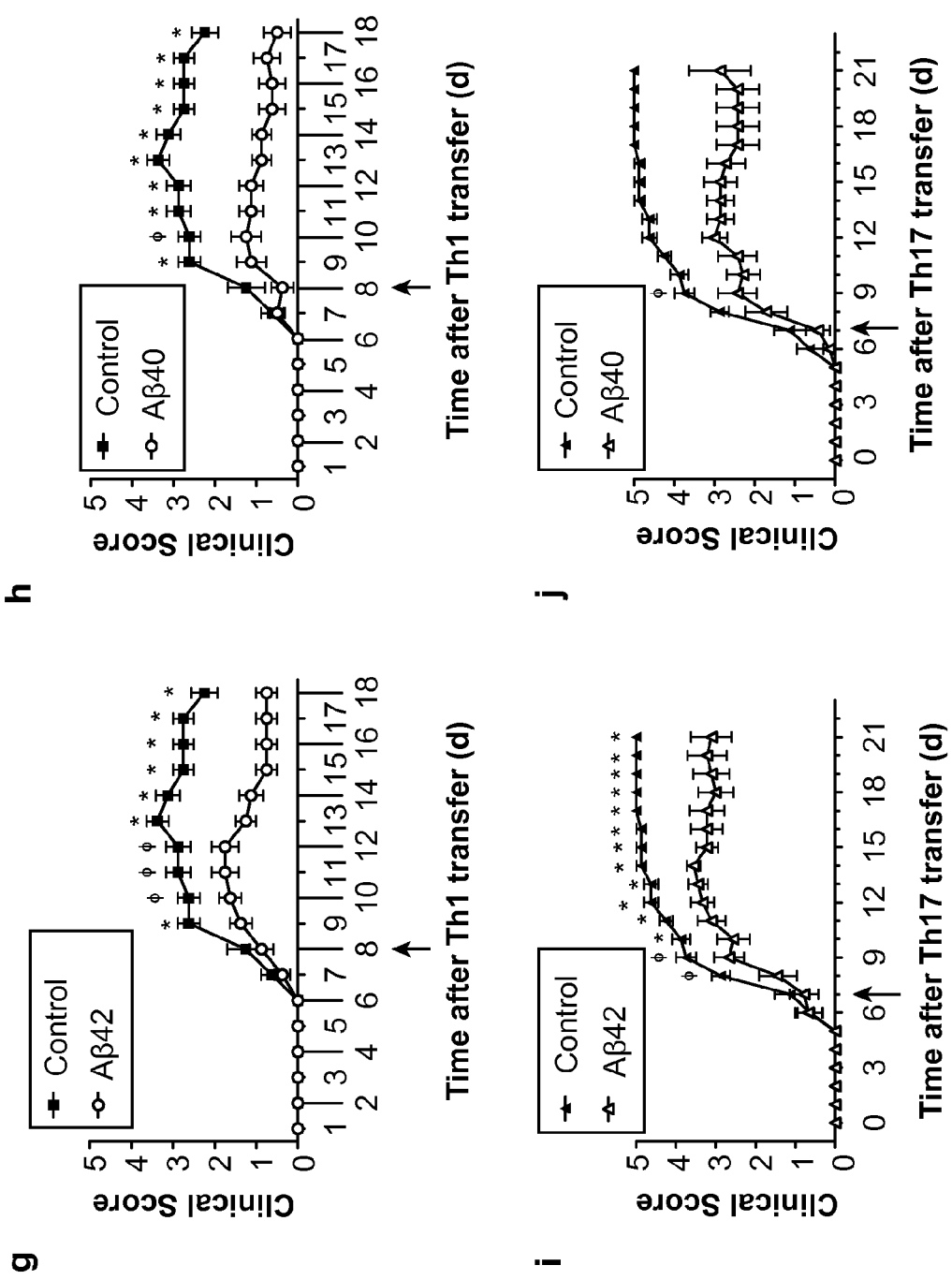
FIG. 3 (Cont. 2)

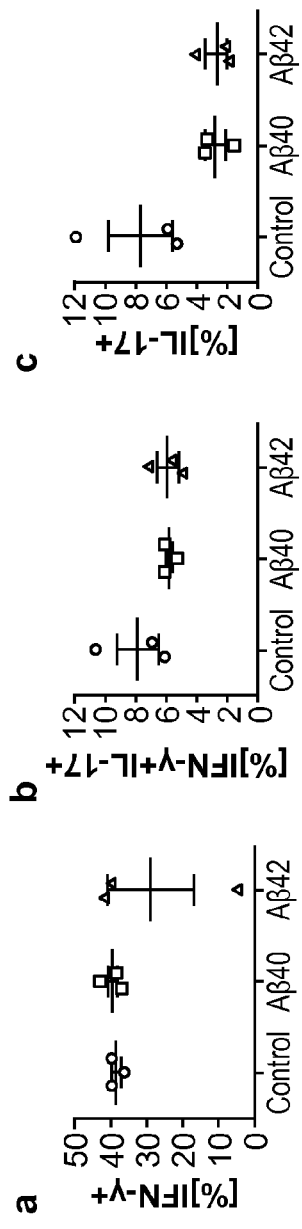
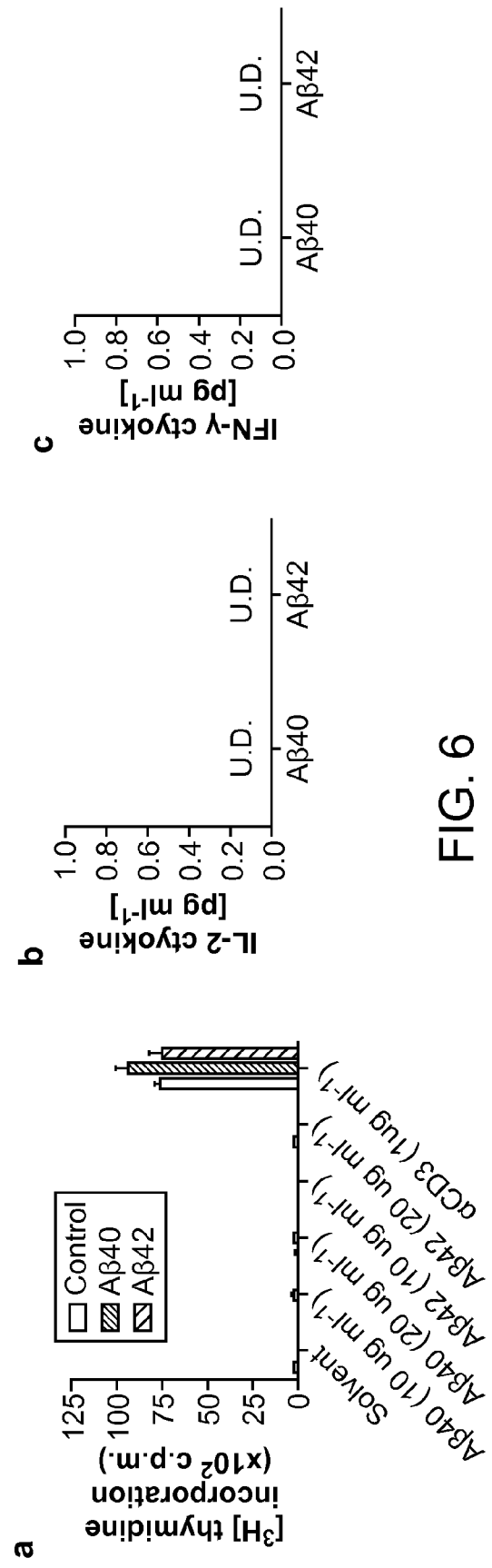
FIG. 5
FIG. 6

| Treatment[b] | Platelet Count[a] [K ul⁻¹] | WBC[a] [K ul⁻¹] | RBC[a] [M ul⁻¹] | Neutrophils[a] [%] | Lymphocytes[a] [%] | Reticulocyte[a] [% ul⁻¹] |
|---|---|---|---|---|---|---|
| Control | 564.7±213.7 | 37.6±4.4 | 8.2±1.1 | 56.7±2.1 | 42.0±1.0 | 0.80±0.2 |
| AB40 | 464.0±259.1 | 45.0±6.9 | 10.1±0.7 | 62.0±7.9 | 36.3±8.3 | 0.67±0.5 |
| AB42 | 570.3±78.2 | 44.0±8.7 | 10.3±2.4 | 63.3±4.6 | 35.3±4.9 | 1.97±1.4 |

The effect of Aβ42 on the immune system is sufficient to ameliorate EAE.

MOG-induced EAE:  TH-induced EAE:

AMYLOID BETA PEPTIDES AS THERAPY FOR MULTIPLE SCLEROSIS

BACKGROUND OF THE INVENTION

Multiple Sclerosis (MS) is an autoimmune disease of the CNS of unknown etiology that affects ~400 000 Americans. In MS, myelin reactive T cells enter into the brain and spinal cord and mediate destruction of the myelin sheath surrounding neurons resulting in progressive motor dysfunction and eventual paralysis. Current treatment strategies include switching the pro-inflammatory Th1 T cell phenotype to an anti-inflammatory Th2 response, preventing encephalitogenic T cells from extravasating into the brain, inducing T cell tolerance, anergy or apoptosis, and repairing or replacing damaged CNS cells, such as neurons and oligodendrocytes.

The course of disease is highly varied and unpredictable. In most patients, especially when MS begins with optic neuritis, remissions can last months to >10 yr. However, some patients have frequent attacks and are rapidly incapacitated, although life span is shortened only in very severe cases.

Goals for therapy include shortening acute exacerbations, decreasing frequency of exacerbations, and relieving symptoms; maintaining the patient's ability to walk is particularly important. Acute exacerbations may be treated with brief courses of corticosteroids. However, although they may shorten acute attacks and perhaps slow progression, corticosteroids have not been shown to affect long-term outcome.

Immunomodulatory therapy decreases frequency of acute exacerbations and delays eventual disability. Immunomodulatory drugs include interferons (IFNs), such as IFN-β1b and IFN-β1a. Glatiramer acetate may also be used. Other potential therapies include the immunosuppressant methotrexate and Natalizumab, an anti-$\alpha_4$ integrin antibody that inhibits passage of leukocytes across the blood-brain barrier. Immunosuppressants such as mycophenolate and cyclophosphamide have been used for more severe, progressive MS but are controversial.

In addition to suppressing the pathological immune response it is important to protect CNS cells from further damage and to induce repair of injured cells since some cells such as neurons have few progenitors in the adult mammalian brain and are thus limiting.

Compositions and methods for treating MS are of great clinical interest. The present invention addresses this issue.

SUMMARY OF THE INVENTION

The invention provides methods for treating inflammatory diseases, including neurological inflammatory diseases, which may be demyelinating autoimmune diseases, such as multiple sclerosis, chronic inflammatory demyelinating polyneuropathy, etc. and the like. The methods of the invention comprise administering to the subject an effective amount of an amyloid beta peptide, including without limitation Aβ42 (SEQ ID NO:1) and Aβ40 (SEQ ID NO:2) or a fragment or derivative thereof, where the dose is effective to suppress or prevent initiation, progression, or relapses of disease, including the progression of established disease. The peptide may be administered by a systemic route, e.g. by injection, and is usually administered in the absence of an adjuvant. In some embodiments the peptide is Aβ40.

Treatment with Aβ42 or Aβ40 peptides in the periphery is shown to confer protection against demyelinating autoimmune disease with attenuation of motor paralysis, reduction of inflammatory lesions in the central nervous system (CNS), and suppression of lymphocyte activation. Aβ40 does not alter immune cell viability, and down-regulates proinflammatory cytokines after systemic administration.

In some methods of the invention, the subject is a human. In some methods, the patient has ongoing inflammatory disease and the method further comprises monitoring a decrease in the symptoms of the patient responsive to the administering of amyloid beta peptide.

BRIEF DESCRIPTION OF THE DRAWINGS

FIG. 5. Effect of Aβ peptides on Th1 and Th17 immune cell infiltration in the CNS during EAE. Frequency, determined by flow cytometry, of IFN-γ+CD4+ (a) IFN-γ+IL-17+CD4+ (b) or IL-17+CD4+ (c) T-cells in the spinal cord of EAE-immunized mice treated with Aβ42 or Aβ40 in prevention paradigm. Assessed 26 days post induction of EAE. (n=3 per treatment group).

FIG. 6. Aβ treatment during EAE does not stimulate an antigen-specific T cell immune response to Aβ. (a,b,c) Splenocytes from MOG35-55 immunized Control-, Aβ42-, or Aβ40-treated mice were re-stimulated in vitro in the presence of Aβ42, Aβ40, or beads coated with αCD3 antibodies (1 ug ml-1) for 72 h to assess activation to Aβ peptides or sufficient T-cell activation. (a) Immune cell activation assessed by thymidine incorporation. Aβ peptide in vitro concentration 10 or 20 ug ml-1. Cytokine secretion of IL-2 (b) and IFN-γ (c) measured by ELISA. (U.D., undetectable). Aβ peptide in vitro concentration 10 ug ml-1. Splenocytes extracted 10 days after EAE induction from mice treated with 100 ug Aβ peptides in prevention paradigm.

DETAILED DESCRIPTION

Figure 1:
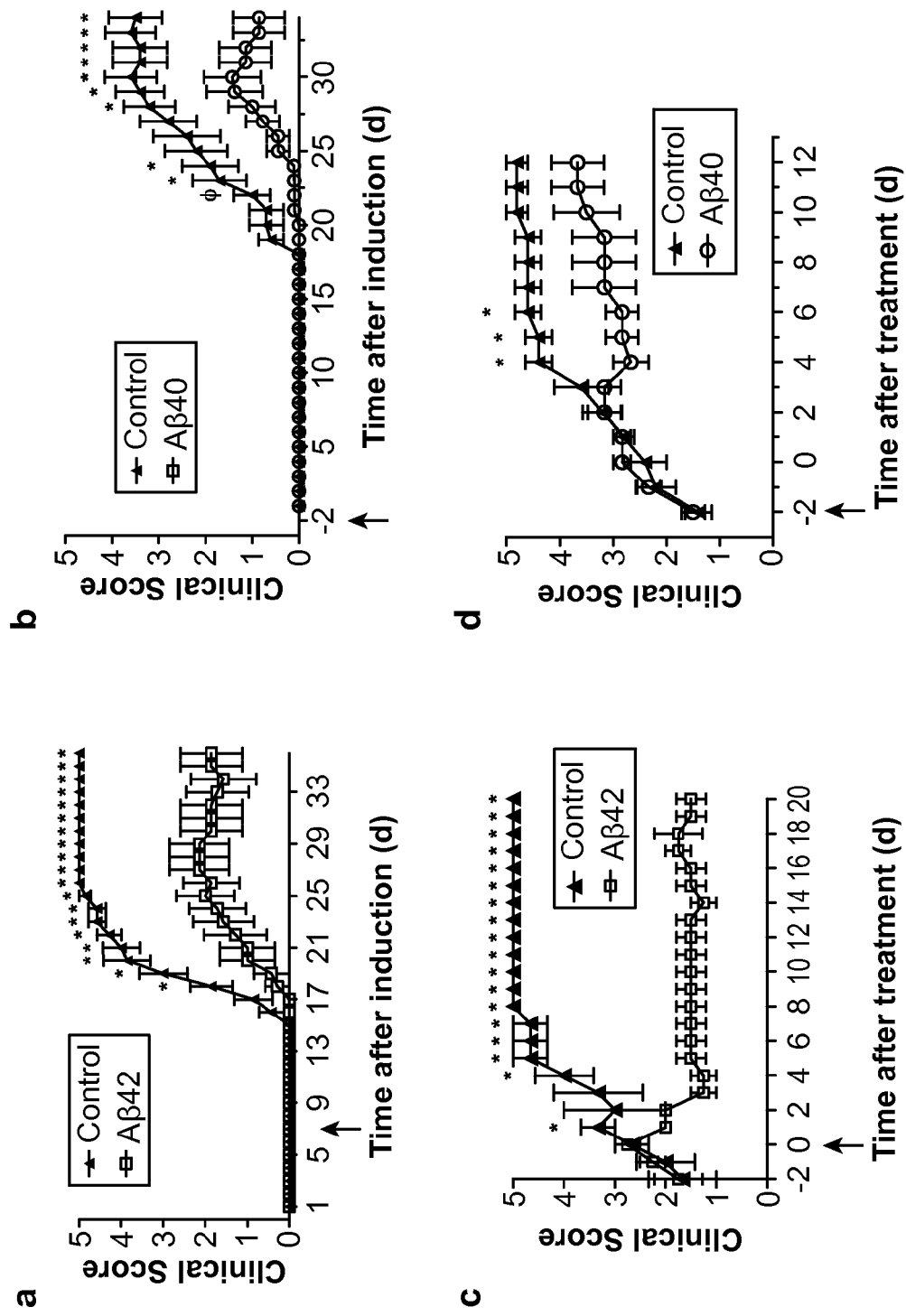
FIG. 1. Aβ42 and Aβ40 peptides attenuate clinical MOG-induced EAE disease progression. (a,b) Mean clinical scores±s.e.m. of MOG-immunized mice treated with Aβ42 (a) or Aβ40 (b) before clinical symptoms in prevention model (n=7-12 mice per group) (φ $P<0.05$; *$P<0.03$). (c,d) Mean clinical scores±s.e.m of MOG-immunized mice treated with Aβ42 (c) or Aβ40 (d) at the onset of motor paralysis in treatment model (n=3-6 mice per group). (c) (*$P<0.05$) (d) (*$P<0.02$). Aβ intraperitoneally administered 3 times per week at 100 or 300 ug per injection. Initiation of treatment is indicated with arrows. Mann-Whitney analysis.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

"Activity" of amyloid beta peptide shall mean any enzymatic or binding function performed by that protein.

"Comparable cell" shall mean a cell whose type is identical to that of another cell to which it is compared. Examples of comparable cells are cells from the same cell line.

"Expressible nucleic acid" shall mean a nucleic acid encoding a nucleic acid of interest and/or a protein of interest, which nucleic acid is an expression vector, plasmid or other construct which, when placed in a cell, permits the expression of the nucleic acid or protein of interest. Expression vectors and plasmids are well known in the art.

"Inhibiting" the onset of a disorder shall mean either lessening the likelihood of the disorder's onset, or preventing the onset of the disorder entirely. In the preferred embodiment, inhibiting the onset of a disorder means preventing its onset entirely. As used herein, onset may refer to a relapse in a patient that has ongoing relapsing remitting disease. The methods of the invention are specifically applied to patients that have been diagnosed with an autoimmune disease. Treatment is aimed at the treatment or prevention of relapses, which are an exacerbation of a pre-existing condition.

"Inhibiting" the expression of a gene in a cell shall mean either lessening the degree to which the gene is expressed, or preventing such expression entirely.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art.

"Amyloid beta peptide" shall mean the peptides set forth in SEQ ID NO:1 and SEQ ID NO:2 and fragments and derivatives thereof. Aβ is the main component of amyloid plaques. Aβ is formed after sequential cleavage of the amyloid precursor protein (APP), a transmembrane glycoprotein of undetermined function. APP can be processed by α-, β- and γ-secretases; Aβ protein is generated by successive action of the β and γ secretases. The γ secretase, which produces the C-terminal end of the Aβ peptide, cleaves within the transmembrane region of APP and can generate a number of isoforms of 36-43 amino acid residues in length. The most common isoforms are Aβ40 and Aβ42; the shorter form is typically produced by cleavage that occurs in the endoplasmic reticulum, while the longer form is produced by cleavage in the trans-Golgi network. The Aβ40 form is the more common of the two, but Aβ42 is the more fibrillogenic.

Amyloid beta is intrinsically unstructured, meaning that in solution it does not acquire a compact tertiary fold but rather populates a set of structures. By NMR-guided simulations, amyloid beta 1-40 and amyloid beta 1-42 also seem to feature highly different conformational states, with the C-terminus of amyloid beta 1-42 being more structured than that of the 1-40 fragment.

Active fragments of amyloid beta peptide share a functional or binding property with full length amyloid beta peptide. Epitopic fragments of amyloid beta peptide bind to a monoclonal antibody that binds to full length amyloid beta peptide.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

The term "inflammatory" response is the development of a humoral (antibody mediated) and/or a cellular (mediated by antigen-specific T cells or their secretion products) response, which may include a component that is directed against amyloid beta peptide. An "immunogen" is capable of inducing an immunological response against itself on administration to a mammal or due to autoimmune disease.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The subject methods are used for prophylactic or therapeutic purposes. As used herein, the term "treating" is used to refer to both prevention of relapses, and treatment of pre-existing conditions. For example, the prevention of autoimmune disease may be accomplished by administration of the agent prior to development of a relapse. The treatment of ongoing disease, where the treatment stabilizes or improves the clinical symptoms of the patient, is of particular interest.

The invention provides methods for treating inflammatory diseases. Inflammatory diseases of interest include neurological inflammatory conditions and demyelinating diseases, such as multiple sclerosis, chronic inflammatory demyelinating polyneuropathy, etc. as well as inflammatory conditions such as rheumatoid arthritis, insulin dependent diabetes mellitus (IDDM, type I diabetes), systemic lupus erythematosis (SLE), Chrohn's disease, celiac disease, etc. The methods of the invention comprise administering to the subject an effective amount of an agent that provides an immunosuppressive dose of amyloid beta peptide activity, to suppress or prevent initiation, progression, or relapses of disease.

Inflammatory disease in a subject is treated by administering to the subject a therapeutically effective amount of an amyloid beta peptide polypeptide, or active fragment or derivative thereof. As shown herein, amyloid beta peptides provide multiple functions that act in the treatment of inflammatory conditions by suppression of activated lymphocytes. Administration of an amyloid beta peptide by a systemic route, i.e. into the periphery, in the absence of adjuvant suppresses activated lymphocytes and reduces penetration of such lymphocytes into the CNS. A$\beta$40 downregulates expression of pro-inflammatory molecules, including eotaxin, G-CSF (granulocyte colony-stimulating factor), IFN-$\gamma$, and IL-12p40. A$\beta$42 has a cytotoxic effect on lymphocytes. The peptides may be administered as a single agent, as a cocktail of both peptides; or in combination with a second therapeutic agent.

In this invention, administering the instant compositions can be effected or performed using any of the various methods and delivery systems known to those skilled in the art. The administering is performed to provide for a systemic administration, usually to contact peripheral lymphocytes, for example, intravenously, intra-peritoneally, via implant, transmucosally, transdermally, intramuscularly, intrathecally, and subcutaneously. Preferably the formulation is free of adjuvants.

Conditions for Analysis and Therapy

The compositions and methods of the invention find use in combination with a variety of inflammatory conditions, including neurological inflammatory conditions, relapsing autoimmune conditions, and relapsing neurological inflammatory conditions.

Immunohistochemical and molecular biological evidence has shown that the brain is capable of sustaining an immune response and that the result may be damaging to host cells. The brain, rather than being immunologically privileged, may be particularly vulnerable since neurons are postmitotic. They cannot divide so that, once lost, they are not replaced. These reactions may involve inflammatory components by local neurons and glia, and especially resident phagocytes—which, in the brain, are the microglia. The complement system, microglia, and inflammatory cytokines appear to play key roles.

Inflammatory neurological diseases include Multiple sclerosis (MS), which is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive (primary progressive MS, PPMS). Relapsing remitting MS (RR MS) is characterized clinically by relapses and remissions that occur over months to years, with partial or full recovery of neurological deficits between attacks. Such patients manifest approximately 1 attack, or relapse, per year. Over 10 to 20 years, approximately 50% of RR MS patients develop secondary progressive MS (SP MS) which is characterized by incomplete recovery between attacks and accumulation of neurologic deficits resulting in increasing disability.

Diagnosis is indirect, by deduction from clinical, radiographic (brain plaques on magnetic resonance [MR] scan), and to a lesser extent laboratory (oligoclonal bands on CSF analysis) features. Typical cases can usually be diagnosed confidently on clinical grounds. The diagnosis can be suspected after a first attack. Later, a history of remissions and exacerbations and clinical evidence of CNS lesions disseminated in more than one area are highly suggestive.

Peripheral neuropathies include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

Rheumatoid Arthritis is a chronic syndrome characterized by usually symmetric inflammation of the peripheral joints, potentially resulting in progressive destruction of articular and periarticular structures, with or without generalized manifestations. The cause is unknown. A genetic predisposition has been identified and, in white populations, localized to a pentapeptide in the HLA-DR beta1 locus of class II histocompatibility genes. Environmental factors may also play a role. Immunologic changes may be initiated by multiple factors. About 0.6% of all populations are affected, women two to three times more often than men. Onset may be at any age, most often between 25 and 50 yr.

Prominent immunologic abnormalities that may be important in pathogenesis include immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Macrophages and their cytokines (e.g., tumor necrosis factor, granulocyte-macrophage colony-stimulating factor) are also abundant in diseased synovium. Increased adhesion molecules contribute to inflammatory cell emigration and retention in the synovial tissue. Increased macrophage-derived lining cells are prominent along with some lymphocytes and vascular changes in early disease.

In chronically affected joints, the normally delicate synovium develops many villous folds and thickens because of increased numbers and size of synovial lining cells and colonization by lymphocytes and plasma cells. The lining cells produce various materials, including collagenase and stromelysin, which can contribute to cartilage destruction; interleukin-1, which stimulates lymphocyte proliferation; and prostaglandins. The infiltrating cells, initially perivenular but later forming lymphoid follicles with germinal centers, synthesize interleukin-2, other cytokines, RF, and other immunoglobulins. Fibrin deposition, fibrosis, and necrosis also are present. Hyperplastic synovial tissue (pannus) may erode cartilage, subchondral bone, articular capsule, and ligaments. PMNs are not prominent in the synovium but often predominate in the synovial fluid.

Onset is usually insidious, with progressive joint involvement, but may be abrupt, with simultaneous inflammation in multiple joints. Tenderness in nearly all inflamed joints is the most sensitive physical finding. Synovial thickening, the most specific physical finding, eventually occurs in most involved joints. Symmetric involvement of small hand joints (especially proximal interphalangeal and metacarpophalangeal), foot joints (metatarsophalangeal), wrists, elbows, and ankles is typical, but initial manifestations may occur in any joint.

Therapeutic Agents

Inflammatory diseases, particularly inflammatory demyelinating neuropathies, are treated by administering to the subject a therapeutically effective amount of an amyloid beta peptide polypeptide, or active fragment or derivative thereof. Administration of an amyloid beta peptide by a systemic route in the absence of adjuvant suppresses activated lymphocytes and reduces penetration of such lymphocytes into the CNS. Aβ40 downregulates expression of pro-inflammatory molecules, including eotaxin, G-CSF (granulocyte colony-stimulating factor), IFN-γ, and IL-12p40. Aβ42 has a cytotoxic effect on lymphocytes. The peptides may be administered as a single agent, as a cocktail of both peptides; or in combination with a second therapeutic agent.

Amyloid beta peptides, which can be used in the methods of the invention, comprise at least about 20 amino acids, usually at least about 30 amino acids, at least about 32 amino acids, at least about 34 amino acids, at least about 36 amino acids, at least about 38 amino acids, at least about 40 amino acids, and which may include up to the complete sequence set forth in SEQ ID NO:1 or SEQ ID NO:2, or modifications thereof, and may further include fusion polypeptides as known in the art in addition to the provided sequences. The amyloid beta peptide sequence may be from any mammalian or avian species, e.g. primate sp., particularly humans; rodents, including mice, rats and hamsters; rabbits; equines, bovines, canines, felines; etc. Of particular interest are the human proteins.

In some embodiments of the invention, the amyloid beta peptide, or a functional fragment thereof is administered to a patient. Amyloid beta peptide useful in this invention also include derivatives, variants, and biologically active fragments of naturally occurring amyloid beta peptides, and the like. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to two, one to five, one to ten, one to twenty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, usually at least about 95%, more usually at least about 99%.

The sequence of amyloid beta peptides as described above may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

Amyloid beta peptides can be further modified, e.g., joined to a wide variety of other oligopeptides or proteins for a variety of purposes. For example, post-translationally modified, for example by prenylation, acetylation, amidation, carboxylation, glycosylation, pegylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, variants of the present invention include variants having phosphorylated amino acid residues, e.g. phosphotyrosine, phosphoserine, or phosphothreonine.

The ability of an amyloid beta peptide to modulate lymphocyte activity can be determined, for example, by the ability of the peptide to have a cytotoxic effect on activated lymphocytes; to downregulate expression of pro-inflammatory cytokines by activated lymphocytes, and the like, as disclosed in the Examples provided herein.

In some embodiments, an amyloid beta peptide of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. These fusion proteins can facilitate purification and show an increased half-life in vivo. Fusion proteins having disulfide-linked dimeric structures (due to the IgG) can also be more efficient in binding and neutralizing other molecules than the monomeric secreted protein or protein fragment alone.

In yet some other embodiments, the second polypeptide is a marker sequence, such as a peptide which facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984. The addition of peptide moieties to facilitate handling of polypeptides are familiar and routine techniques in the art.

In some other embodiments, amyloid beta peptide variants of the present invention include variants further modified to improve their resistance to proteolytic degradation or to optimize solubility properties or to render them more suitable as a therapeutic agent. For example, variants of the present invention further include analogs containing residues other than naturally occurring L-amino acids, e.g. D-amino acids or non-naturally occurring synthetic amino acids. D-amino acids may be substituted for some or all of the amino acid residues.

Variants of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The polypeptides may be prepared by cell-free translation systems, or synthetic in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

According to the present invention, an amyloid beta peptide can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, pharmaceutical compositions of the present invention include one or more therapeutic entities of the present invention in combination with another therapeutic agent.

Therapeutic entities of the present invention are often administered as pharmaceutical compositions comprising an active therapeutic agent and a other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

The method also provide for combination therapy, where the combination may provide for additive or synergistic benefits. Combinations of an amyloid beta peptide may be obtained with a second agent selected from one or more of the general classes of drugs commonly used in the non-antigen specific treatment of autoimmune disease, which include corticosteroids and disease modifying drugs; or from an antigen-specific agent. Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

Disease modifying drugs take several weeks or months to demonstrate a clinical effect. These agents include methotrexate, leflunomide (Arava™), etanercept (Enbrel™) infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like. Treatments for MS, which are optionally combined therapeutically with an amyloid beta peptide treatment of the invention, include interferon β (Avonex, Betaseron, Rebif), Copaxone (Glatiramer acetate), and anti-VLA4 (Tysabri, natalizumab), which reduce relapse rate. MS is also treated with immunosuppressive agents including methylprednisolone, other steroids, methotrexate, cladribine and cyclophosphamide. Many biological agents, such as anti-IFNγ antibody, CTLA4-Ig (Abetacept), anti-CD20 (Rituxan), and other anti-cytokine agents are in clinical development for MS.

Combination therapies may be sequentially staged, provided in a co-administration formulation, or concomitant administration during the same time period. "Concomitant administration" of a known therapeutic drug with a pharmaceutical composition of the present invention means administration of the drug and amyloid beta peptide at such time that both the known drug and the composition of the present invention will have a therapeutic effect. Such concomitant administration may involve concurrent (i.e. at the same time), prior, or subsequent administration of the drug with respect to the administration of a compound of the invention. A person of ordinary skill in the art would have no difficulty determining the appropriate timing, sequence and dosages of administration for particular drugs and compositions of the present invention.

Antigen specific therapeutic methods include administration of an antigen or epitope specific therapeutic agent. One method to induce immune tolerance is tolerizing DNA vaccines (Garren et al. (2001) Immunity, 15:15-22; Robinson et al. (2003) Nature Biotechnology 21:1033-9). Tolerizing DNA vaccines are DNA plasmids containing the regulatory regions necessary for expression of the encoded cDNA in mammalian cells, and would be engineered to contain cDNA sequence encoding all or a portion of an antigen in order to induce immune tolerance to the encoded epitopes. To enhance the ability of such plasmids to induce immune tolerance, the immunostimulatory CpG sequences (Krieg et al. (1998) Trends Microbiol. 6:23-27) can be reduced in number or completely removed from the plasmid vector. Additionally, immunoinhibitory GpG sequences can be added to the vector (see Ho et al. (2005) J. Immunology, 175:6226-34).

As an alternative, or in addition to DNA tolerization, specific peptides, altered peptides, or proteins may be administered therapeutically to induce antigen-specific tolerance to treat autoimmunity. Native peptides targeted by the autoimmune response can be delivered to induce antigen-specific tolerance (Science 258:1491-4). Native peptides have been delivered intravenously to induce immune tolerance (J Neurol Sci. 152:31-8). Delivery of peptides that are altered from the native peptide, is also known in the art. Alteration of native peptides with selective changes of crucial residues (altered peptide ligands or "APL") can induce unresponsiveness or change the responsiveness of antigen-specific autoreactive T cells. In another embodiment, whole protein antigens targeted by the autoimmune response can be delivered to restore immune tolerance to treat autoimmunity (Science 263:1139).

Pharmaceutical Compositions

Amyloid beta peptides serve as the active ingredient in pharmaceutical compositions formulated for the treatment of various disorders as described above. The active ingredient is present in a therapeutically effective amount, i.e., an amount sufficient when administered to treat a disease or medical condition mediated thereby, in particular by reducing the activity of inflammatory lymphocytes. The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

The peptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal method.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

The amyloid beta peptide compositions may be administered in a single dose, or in multiple doses, usually multiple doses over a period of time, e.g. daily, every-other day, weekly, semi-weekly, monthly etc. for a period of time sufficient to reduce severity of the inflammatory disease, which may comprise 1, 2, 3, 4, 6, 10, or more doses.

Determining a therapeutically or prophylactically effective amount can be done based on animal data using routine computational methods. In one embodiment, the therapeutically or prophylactically effective amount contains between about 0.1 mg and about 1 g of protein. In another embodiment, the effective amount contains between about 1 mg and about 100 mg of protein. In a further embodiment, the effective amount contains between about 10 mg and about 50 mg of the protein. The effective dose will depend at least in part on the route of administration. The dose may be from about 0.1 μg/kg patient weight; about 1 μg/kg; about 10 μg/kg; to about 100 μg/kg.

Treating, treatment, or therapy of a disease or disorder shall mean slowing, stopping or reversing the disease's progression by administration of an amyloid beta peptide composition. In the preferred embodiment, treating a disease means reversing the disease's progression, ideally to the point of eliminating the disease itself. As used herein, ameliorating a disease and treating a disease are equivalent. Preventing, prophylaxis or prevention of a disease or disorder as used in the context of this invention refers to the administration of an amyloid beta peptide composition to prevent the occurrence or onset of a disease or disorder or some or all of the symptoms of a disease or disorder or to lessen the likelihood of the onset of a disease or disorder.

This invention will be better understood by reference to the Examples which follow, but those skilled in the art will readily appreciate that the information detailed is only illustrative of the invention as described more fully in the claims which follow thereafter.

EXPERIMENTAL

Example 1

Unexpected Protective Role of Amyloid-β in Th1- and Th17-Induced Central Nervous Extracellular amyloid-beta (Aβ) plaques are a primary pathological hallmark of Alzheimer's disease (AD). It is widely accepted, based on pathology, biochemistry, and genetics, that Aβ accumulation is critical to neurodegeneration in AD. In fact, major efforts are underway to reduce production or enhance clearance of Aβ as a therapy for the disease. Yet molecules are often poised for polar roles, causing damage in some contexts, yet providing benefit and protection in others. The Janus-like faces of Aβ become apparent when studying its role in autoimmune inflammatory diseases of the brain, where we find that it provides benefit and protects from autoimmune mediated damage induced by encephalitogenic CNS peptides or proinflammatory Th1 and Th17 cells.

Aβ is produced from proteolytic cleavage of amyloid precursor protein (APP) by β- and γ-secretase enzymes, which yield various amino acid sequences of amyloid-β, including 42- and 40-residue Aβ peptides (Aβ42 and Aβ40, respectively). At normal physiological conditions, Aβ40 is present at ten-fold higher levels compared to Aβ42 in the CNS. Aβ42 is upregulated during injury, inflammation, and stress in the brain. Aβ is also present in plasma at lower concentrations and is in dynamic equilibrium with Aβ in the brain. Within and around Aβ senile plaques in AD, activated microglia, astrogliotic astrocytes, components of the classical complement pathway, and cytokines such as TGF-β, TNF-α, IL-1β are all present. The association of Aβ with these hallmarks of innate inflammation has implied that these peptides may actually contribute or even orchestrate the destruction of neurons in AD.

In multiple sclerosis (MS), demyelinating areas called plaques are comprised, in part, of lymphocytes and bone marrow-derived macrophages that have infiltrated the CNS, resulting in axonal damage. Aβ is upregulated in acute and chronic MS lesions and is a sensitive immunohistochemical marker of axonal damage. We noted previously that an N-terminus epitope shared by Aβ40 and Aβ42 is a target of antibody responses in cerebrospinal fluid samples from patients with relapsing remitting MS, suggesting that Aβ is a target of the inflammatory response in the disease. We also reported that Aβ is elevated in laser captured microdissected lesions from MS brain, analyzed with mass spectroscopy and proteomics. In order to understand the function of Aβ in inflammatory demyelinating disease, we explored its role in various forms of experimental autoimmune encephalomyelitis (EAE), considered an animal model of MS.

Due to the proinflammatory properties of Aβ deposition in AD, we hypothesized that Aβ treatment during EAE would worsen disease due to the induction of proinflammatory, macrophage-driven immune responses or Aβ-specific T-cell activation. C57BL/6 mice with $MOG_{35-55}$-induced EAE were treated with Aβ42, Aβ40 or solvent control 3-times per week by intraperitoneal injection prior to clinical disease onset (prevention paradigm). Animals were scored daily for signs of disease based on a graded 0-5 score for ascending motor paralysis. To our surprise, treatment with Aβ42 and Aβ40 peptides significantly delayed the onset of EAE symptoms and reduced the severity and incidence of disease (FIG. 1A and FIG. 1B). Next we tested whether Aβ-treatment could reverse the progression of EAE after the onset of symptoms (treatment paradigm). We found that Aβ42- and Aβ40-treatment attenuated motor paralysis compared to control EAE mice (FIG. 1C and FIG. 1D). Aβ42-treatment reversed motor paralysis after 2 days and Aβ40-treatment reduced disease severity after 4 days. Both Aβ-peptides continued to confer protection for the remainder of the experiment.

To determine whether the protective effect was not unique to the MOG-057BL/6 model, we treated mice with the relapsing-remitting model of EAE. SJL/J mice were injected with $PLP_{139-151}$ and treated with Aβ42 in the prevention paradigm. Aβ42-treatment conferred a trend for clinical protection in attenuating motor paralysis in SJL/J mice [EAE Score: Control (3.3±0.4), Aβ42 (1.8±0.7), p=0.08, Day 23]. The clinical effect in this strain may reflect the spontaneous relapsing and remitting nature of this model, as compared to the progressive EAE model in C57B1/6 mice. Treatment significantly reduced inflammation in the CNS and modulated immunological manifestations of CNS damage in paralyzed mice, compared to mice receiving vehicle.

Figure 2:
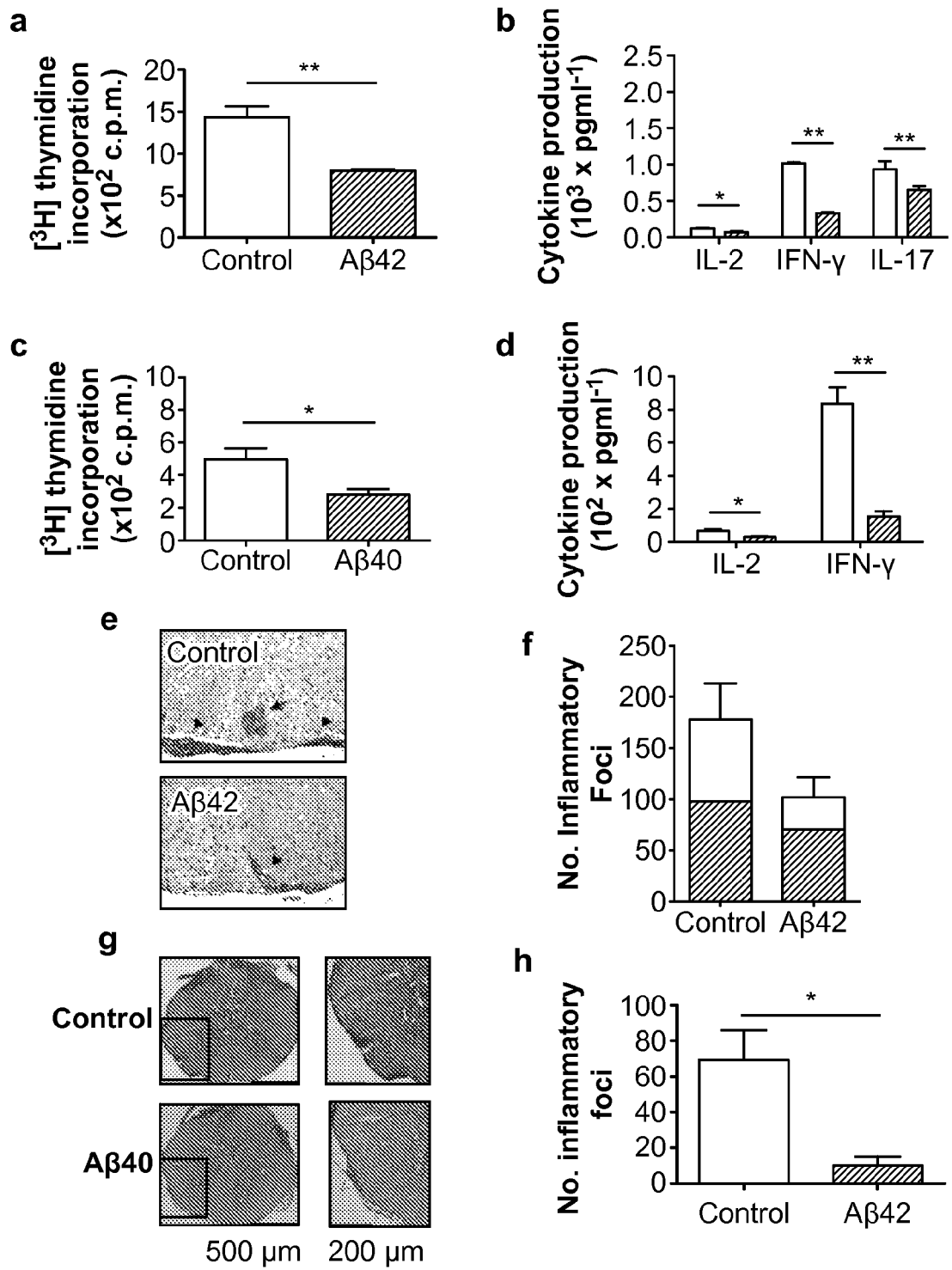
FIG. 2. In vivo Aβ42 and Aβ40 treatment suppress inflammation and reduce CNS lesions in EAE. (a-d) In vitro myelin recall responses of spleen and lymph nodes from EAE mice treated in vivo with solvent control (black), Aβ42 (blue) or Aβ40 (green) three times per week in prevention model (100 ug). (a,c) Thymidine incorporation. (b,d) Quantification of proinflammatory cytokine production by ELISA. Interleukin (IL)-2, interferon (IFN)-γ, IL-17. Representative of 48, 72, 96 h timepoints. (*$P<0.05$; $P<0.01$). (e) Histology of dorsal motor horn spinal cord sections and (f) quantification of inflammatory foci, meningeal (dark shading), parenchymal (light shading), from Aβ42-treated mice 34 days after EAE induction. Parenchymal foci (arrow), meningeal foci (arrowheads). Sections stained with H&E. (g) Histology and (h) quantification of spinal cord sections from Aβ40-treated mice 21 days after EAE induction. Sections stained with H&E and Luxol Fast Blue. ($P<0.03$). Error bars show s.e.m.

Examination of myelin-specific lymphocyte responses to the immunizing peptide revealed decreased antigen-specific cell proliferation in secondary lymphoid tissues (FIG. 2A and FIG. 2C) and inhibition of the pro-inflammatory cytokines interleukin (IL)-2, IL-6, interferon (IFN)-γ, and IL-17 (FIG. 2B and FIG. 2D) following in vivo administration of either Aβ42 or Aβ40. Cytokines assessed are considered pro-inflammatory and include key components of the well-known Th1 and Th17 pathways, which have a major role in EAE pathogenesis. Concordant with disease attenuation, histological characterization of CNS tissue revealed fewer inflammatory foci in the brain and spinal cords of Aβ42- (FIG. 2E and FIG. 2F) and Aβ40-treated mice (FIG. 2G and FIG. 2H).

Autoreactive Th1 and Th17 immune responses have been associated with relapses and disease severity in MS and animal models of CD4+ T-cell mediated EAE. Therefore, we assessed the amount of IFN-γ and IL-17 produced by infiltrating CD4+ T-cells in the spinal cord at the peak of disease in the C57BL/6 prevention model. There was a decreased frequency of CD4+ T-cells producing IL-17 in the spinal cord in Aβ42- and Aβ40-treated mice compared to solvent-treated mice (FIG. 5A). In contrast, neither of the Aβ-treatments affected the frequency of CD4+ T-cells producing IFN-γ or producing both IFN-γ and IL-17 (FIG. 5B and FIG. 5C).

Therapeutic approaches utilizing active and passive immunization against Aβ for the treatment of AD have highlighted the immunogenic properties of Aβ when paired with an immunizing adjuvant. In fact, active immunization against Aβ in human clinical trials caused meningoencephalitis, suggesting that an autoimmune T-cell response is triggered with active immunization to Aβ. To begin addressing the possibility that repeated Aβ-treatment during EAE initiated a T-cell response against Aβ, we assessed lymphocyte responsiveness to Aβ ten days after MOG-induced EAE in the prevention model. Splenocytes taken from both Aβ42- and Aβ40-treated mice showed negligible thymidine incorporation and cytokine production when restimulated in culture with either Aβ peptide, but they did proliferate following αCD3 stimulation, indicating that the T-cells were capable of activation after Aβ-treatment (FIG. 6A-C). Thus, Aβ treatment during EAE did not elicit a T-cell response to Aβ peptides.

Figure 3:
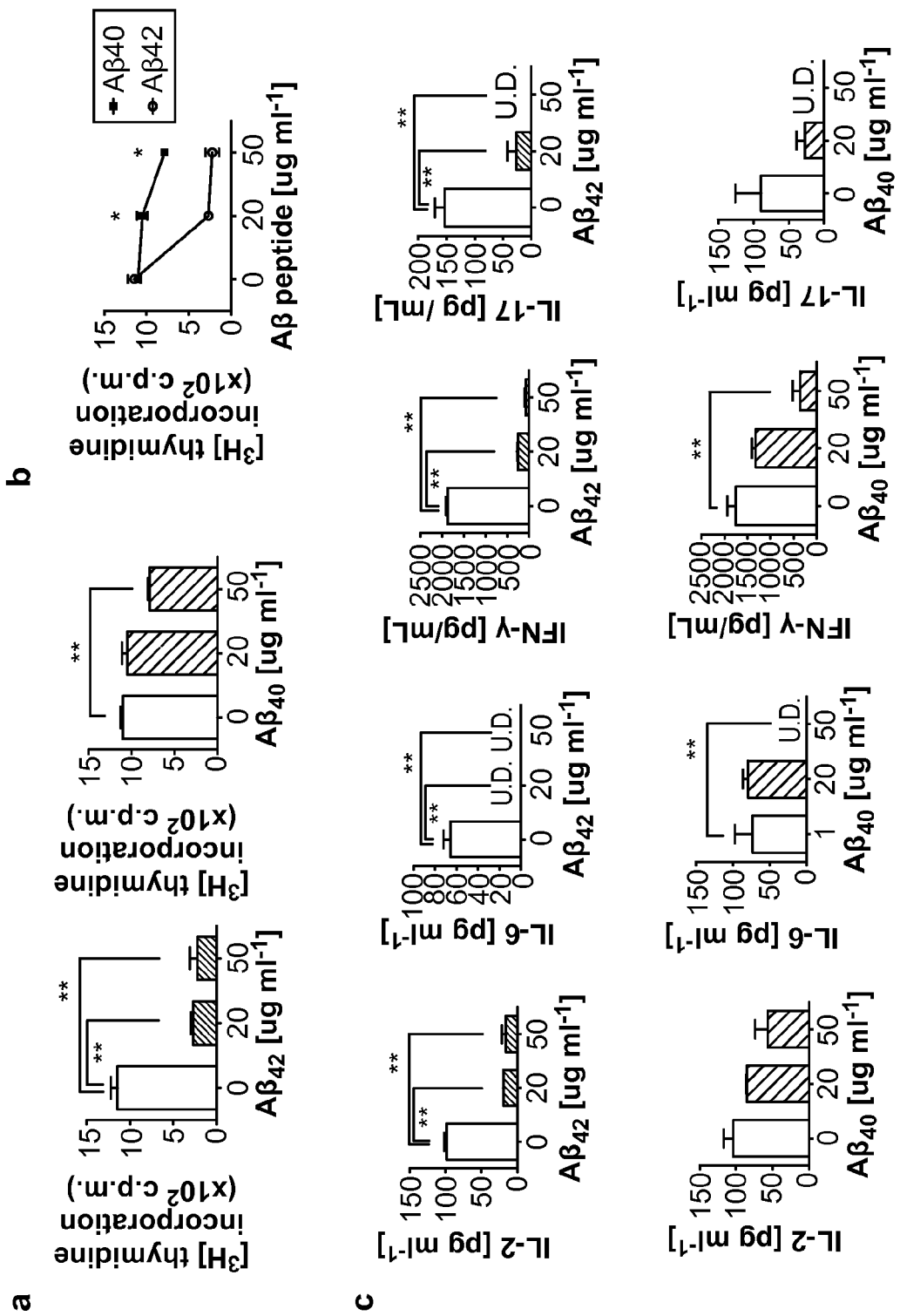
FIG. 3. Aβ42 and Aβ40 suppress mouse and human T lymphocyte function and protect against Th1- and Th17-induced EAE. (a,b) Proliferation of splenocytes stimulated by αCD3 αCD28 with Aβ42 (blue), Aβ40 (green) or solvent control. (b) Direct comparison of proliferation rates. Aβ42 (black) or Aβ40 (white). Proliferation measured by thymidine incorporation. (*$P<0.05$; **$P<0.001$) (c) Quantification of proinflammatory cytokines secreted by activated splenocytes cultured with Aβ42 (blue), Aβ40 (green), or control by ELISA. Cytokines characteristic of T-cells (IL-2), antigen-presenting cells (IL-6), CD4+ Th1 (IFN-γ), or CD4+ Th17 cells (IL-17). Stimulated with (3 ug ml-1) αCD3 αCD28 for 72 h. (*$P<0.02$; **$P<0.001$) (U.D., undetectable) (d) Proliferation rates of activated naïve human CD4+ T-cells cultured with Aβ42 (black) or Aβ40 (white). (e,f) Percent fold change of proinflammatory cytokines (IL-2, IFN-γ) or anti-inflammatory cytokines (IL-10) secreted by human CD4+ T-cells treated with Aβ42 (e) or Aβ40 (f), normalized against internal control. Naïve human CD4+ T-cells isolated from PBMCs by magnetic microbead positive selection and activated with αCD3 αCD28 αCD2 beads for 5 d. (*$P<0.05$; **$P<0.03$). (g-j) Clinical scores of Th1 (g,h) or Th17 (i,j) induced EAE. Recipient mice treated three times per week with Aβ42 (g,i) or Aβ40 (h,j). Initiation of treatment is indicated with arrows. (φ $P<0.04$; *$P<0.01$). (n=7-8 per group). Error bars represent means±s.e.m.

CD4+ T effector cells play a central role in EAE pathology and MS. Transfer of myelin-specific CD4+ T-cells can induce EAE in naïve recipients. Since deleting CD4+ T-cells in EAE inhibits the development of clinical symptoms, we speculated that Aβ treatment might directly inhibit T-lymphocyte function. To explore this hypothesis, C57BL/6 spleen cells were stimulated in vitro with αCD3, αCD28 antibodies and cultured with Aβ42, Aβ40, or solvent control. Both Aβ42 and Aβ40 directly inhibited thymidine incorporation of activated lymphocytes in vitro (FIG. 3A). A direct comparison of thymidine proliferation rates of Aβ42- or Aβ40-treated immune cells revealed that Aβ42 is a more potent inhibitor of immune cell function (FIG. 3B). At 50 μg $ml^{-1}$, Aβ42 induces a 5-fold reduction while Aβ40 induces a 1.4-fold reduction in thymidine incorporation. Production of various proinflammatory cytokines were significantly decreased with titrated concentrations of Aβ42 and Aβ40 in vitro (FIG. 3C).

To extend the observed effects of Aβ42 and Aβ40 in suppressing mouse T-cell function, we isolated naïve human CD4+ T-cells from buffy coat samples of healthy donors. Cells were activated in vitro with beads coated with antibodies to CD2, CD3, and CD28 and cultured with titrated concentrations of Aβ42 or Aβ40 peptides for 5 days. Consistent with our findings in mice, Aβ42 and Aβ40 suppressed proliferation of stimulated human CD4+ T-cells, as measured by thymidine incorporation, in a dose-dependent manner compared to solvent control (FIG. 3D). At 50 μg $ml^{-1}$, Aβ42 reduced proliferation by 56% and Aβ40 reduced proliferation by 43%, compared to control rates. Aβ42 and Aβ40 treatment also significantly reduced secretion of proinflammatory cytokines IL-2, IFN-γ, as well as IL-10, which has both pro and anti-inflammatory attributes (FIG. 3E and FIG. 3F).

Figure 7:
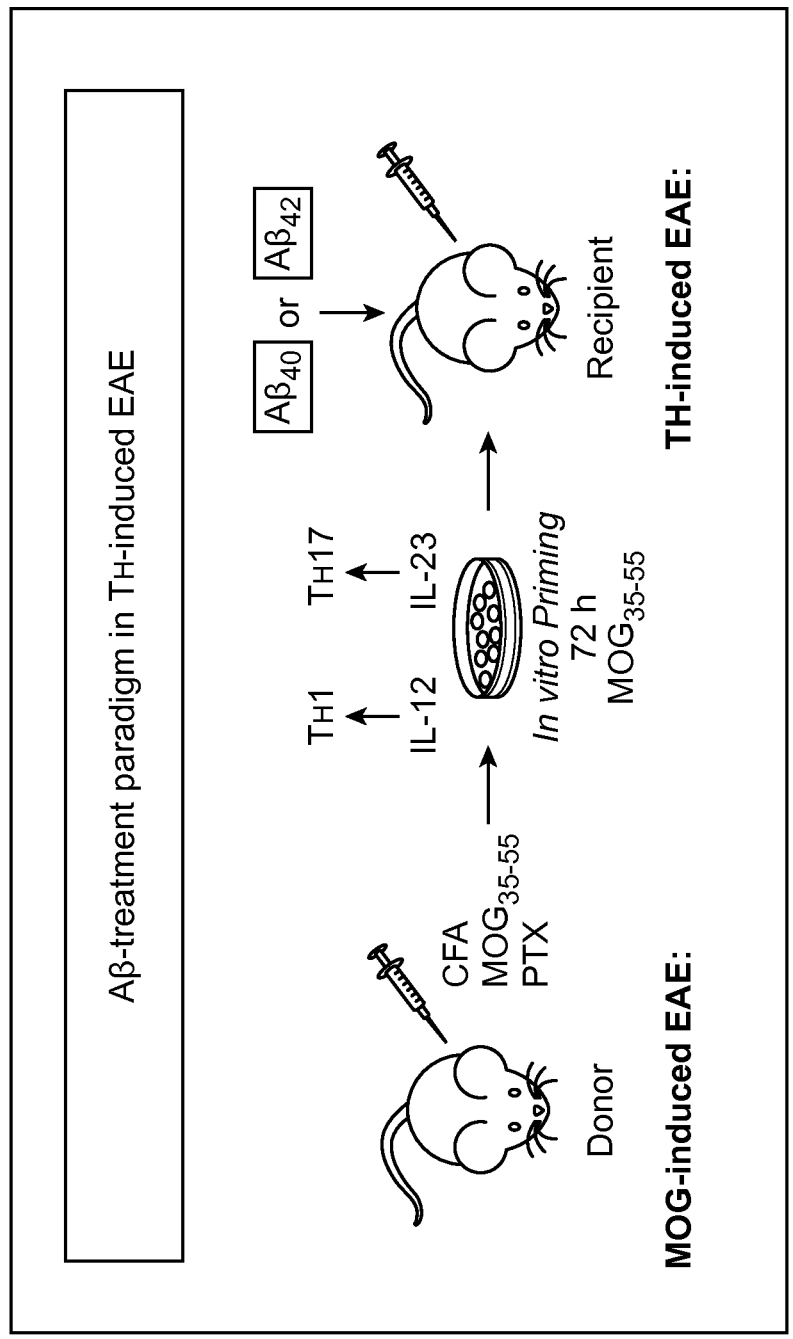
FIG. 7. Schematic of Aβ-treatment paradigm in Th1- and Th17-induced EAE.
Figure 8:
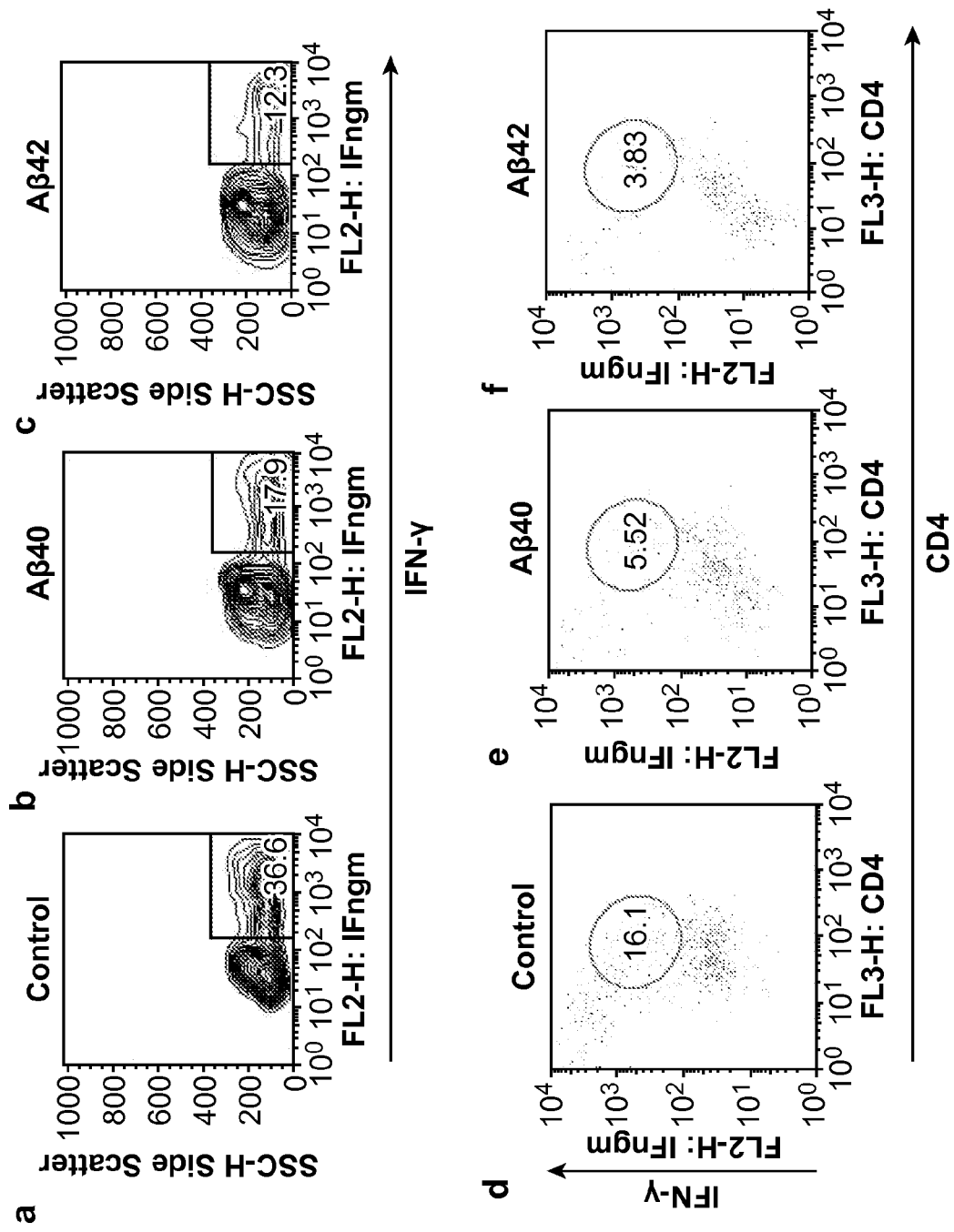
FIG. 8. Aβ peptides inhibit IFN-γ production and CD4+ IFN-γ+ infiltration in the CNS during Th1-induced EAE. Frequency, determined by flow cytometry, of IFN-γ production (a-c) or CD4+IFN-γ+ Th1 cells (d-f) in the spinal cords of Th1-induced EAE recipient mice treated with solvent control, Aβ40 or Aβ42 peptides. Assessed 18 days post adoptive transfer of Th1 cells. Representative frequency plots of n=4 per group.

Thus, our in vitro experiments demonstrate that activated mouse and human CD4+ T-cells are direct targets of Aβ-immunosuppression. Based on these results we tested whether Aβ peptides would be effective in treating EAE induced by adoptive transfer of proinflammatory CD4+ Th1 or Th17 cells (FIG. 7). Either Aβ42 or Aβ40 was administered three times per week starting 7 or 8 days after recipient mice received $MOG_{35-55}$-autoreactive Th1 or Th17 cells. Both Aβ peptides significantly attenuated the progression of EAE symptoms induced by Th1 and Th17 cells in recipient mice (FIG. 3G-J), demonstrating that Aβ can suppress T-cell mediated damage against the CNS in vivo. In accordance with the clinical course of Th1-induced EAE, flow cytometry analysis revealed that Aβ42 and Aβ40 peptides decreased IFN-γ production, a prototypical Th1 cytokine, in the spinal cords of recipient EAE mice (FIG. 8).

Figure 9:
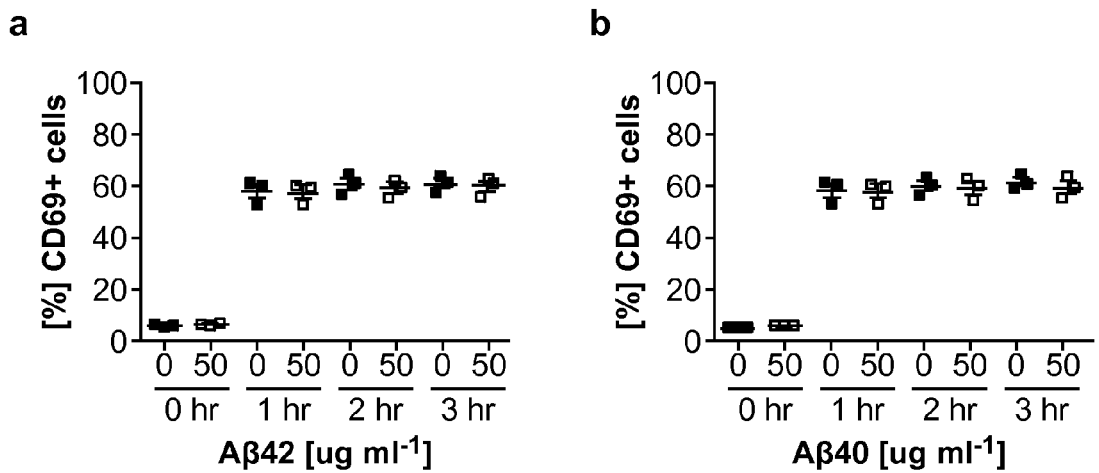
FIG. 9. Aβ peptides do not affect upregulation of CD69 expression during CD4+ T-cell activation. Spleen cells of C57BL/6 mice were stimulated with beads coated with antibodies against CD3,CD28 in the presence of Aβ42 (a) or Aβ40 (b) peptides or DMSO/PBS Solvent Control for 0, 1, 2, and 3 h. CD69 expression in CD4+ T-cells was assessed by flow cytometry. Results are representative of three experiments. (n=3 per treatment group).

We examined several mechanisms by which Aβ peptides suppress T-lymphocyte function to attenuate EAE and discovered that Aβ42 and Aβ40 confer protection by different mechanisms. Since we found that Aβ42 and Aβ40 suppress proliferation of T-cells, we assessed their effects on early events downstream of T-cell activation. Cell surface levels of CD69 are rapidly elevated after TCR engagement and CD69 is an early indicator of T-cell activation. Therefore, we assessed whether Aβ42 or Aβ40 would affect the expression of CD69 on the surface of in vitro activated CD4+ T-cells. We found that Aβ peptides did not alter cell-surface CD69 expression of CD4+ T-cells after 1 to 3 hours of αCD3 stimulation, assessed by FACS (FIG. 9A and FIG. 9B), indicating that Aβ peptides do not suppress early events of T-cell activation.

Figure 4:
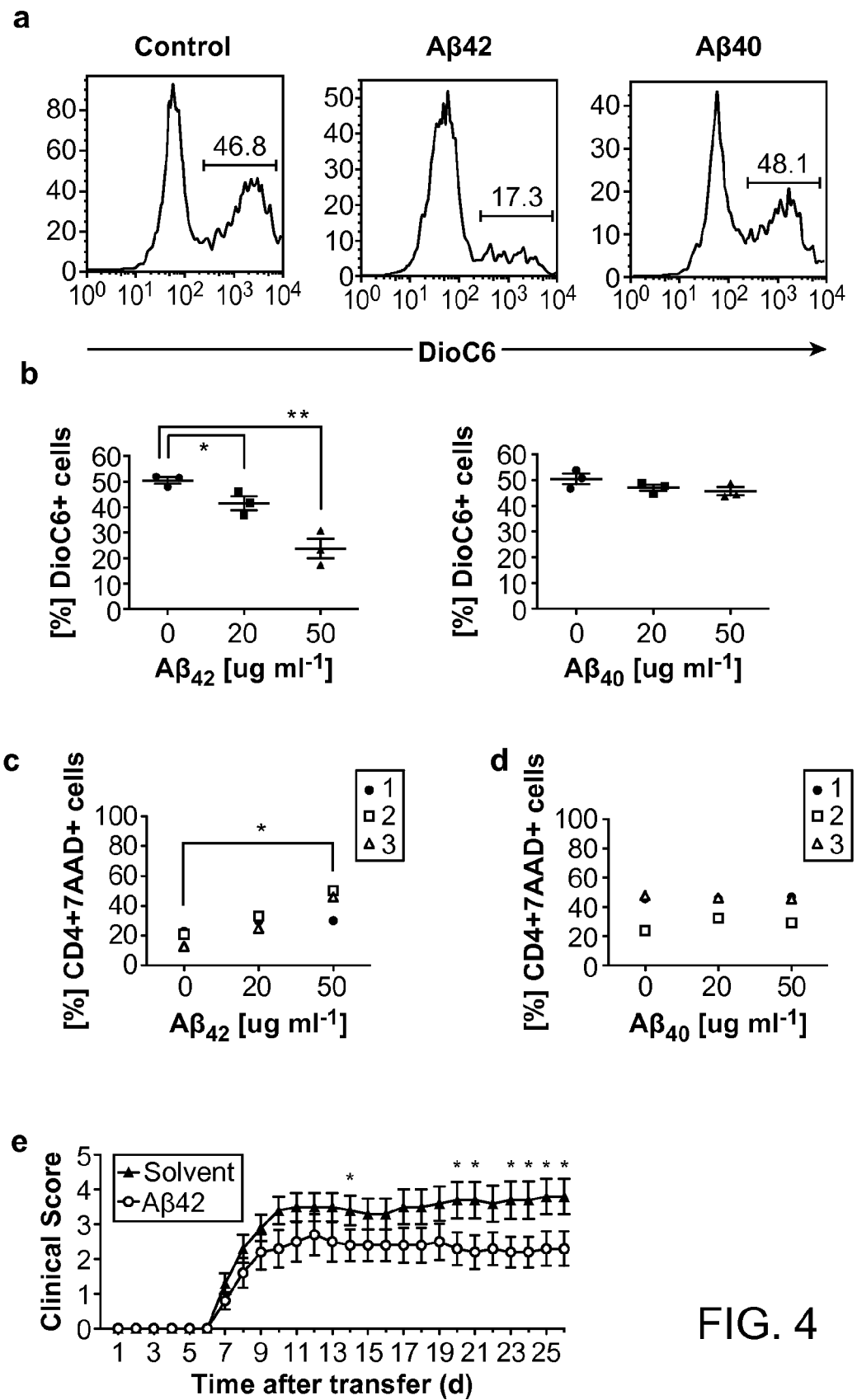
FIG. 4. Aβ42 and Aβ40 differentially suppress autoimmunity. Histogram plots (a) and quantification (b) of frequency of viable mouse CD4+ T-cells expressing DioC6high cultured with Aβ42, Aβ40, or solvent control (50 ug ml-1). Mouse splenocytes activated in vitro with αCD3 (1 ug ml-1). Representative of 48 and 72 h stimulation of three separate experiments. Error bars show s.e.m. (n=3 per group). (*P<0.05; **P<0.01). (c) Frequency of nonviable (7-AAD+) human CD4+ T-cells treated with Aβ42 (c) or Aβ40 (d). PBMCs collected from blood of healthy human donors. Activated by αCD3 αCD28 αCD2 stimulation for 5 d. (*P<0.04) (e) Peripheral immune cells taken from MOG-immunized donor C57BL/6 mice treated with Aβ42 or solvent control for 10 days and adoptively transferred into untreated naïve recipient C57BL/6 mice. EAE induced adoptively in naïve recipients is shown as mean clinical score (n=10 per group) (*P<0.05). (f) Cytokine profiles from EAE-induced mice treated with Aβ42 (purple) or Aβ40 (blue) in prevention model. Sera collected from peripheral blood on EAE Day 10. Relative cytokine depicted as the difference in relation to control EAE mice. Samples analyzed by hierarchical clustering and shown as a heat map where red represents increased amounts, black represents similar amounts, and green represents decreased amounts of cytokine compared to solvent-treated EAE controls. (g) Mean clinical scores of Th17-induced EAE in WT and APP−/− mice (n=7-8 per group). (φ P<0.08, *P<0.05). Error bars represent means±s.e.m.
Figure 4:
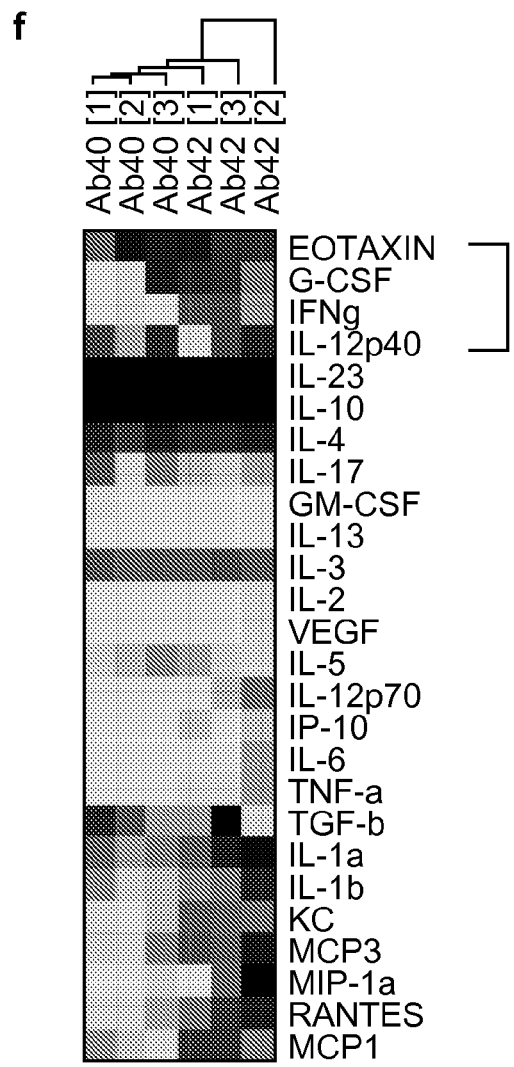
Figure 4:
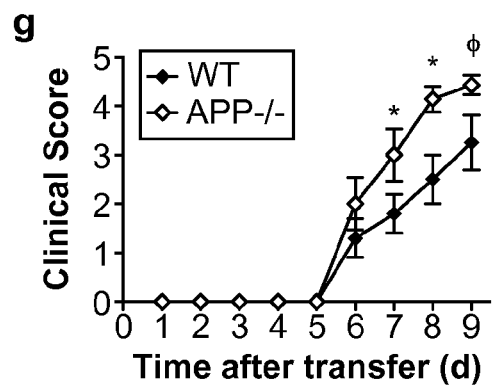
Figure 10:
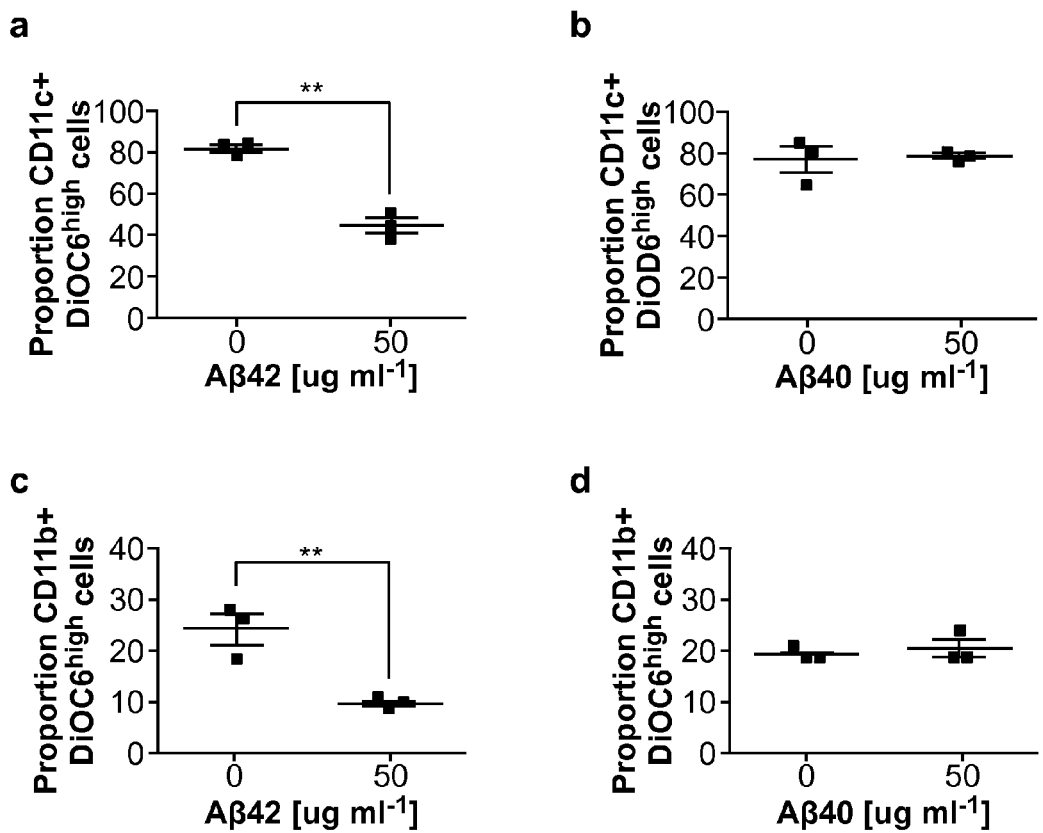
FIG. 10. Differential effects of Aβ42 and Aβ40 on myeloid cell viability. Spleen cells from C57BL/6 mice stimulated with LPS in the presence or absence of Aβ42 (a,c) or Aβ40 (b,d) peptides for 72 hours at 50 ug ml-1. Gated on CD11c+ dendritic cells (a,b) and CD11b+ macrophages (c,d) using respective cell-surface fluorescent markers. Cell viability assessed by DioC6 incorporation to discriminate DiOC6high (viable) and DiOC6low (nonviable) populations by flow cytometry. (n=3 per treatment group).

Due to widespread suppression of proinflammatory cytokines and reduced proliferative capacity of lymphocytes after Aβ treatment, we speculated that Aβ peptides influence lymphocyte viability. In the context of AD, Aβ42 has a well-characterized role in neurodegeneration and has been implicated in inducing excitotoxicity and oxidative stress on neurons. To determine whether immunosuppression was due to Aβ-induced cell death, we assessed cell viability of activated CD4+ T-cells incubated with Aβ42 and Aβ40 by FACS. Using DiOC6, a lipophilic dye that selectively targets intact mitochondrial membranes, we were able to discriminate viable ($DiOC6^{high}$) from nonviable ($DiOC6^{low}$) populations. Aβ42-treatment of activated splenic cells in vitro revealed a significant decrease in viable CD4+ T-cells (FIG. 4A and FIG. 4B). Interestingly, there were no significant changes in the frequency of viable CD4+ T-cells when exposed to Aβ40 in vitro. We confirmed this observation with human T-cells and observed that Aβ42 treatment significantly increased the frequency of nonviable 7AAD+ human CD4+ T-cells compared to untreated cultures (FIG. 4C). The frequency of dead cells increased from 18.9% to 42.0% when human CD4+ T-cells were cultured with 50 μg $ml^{-1}$ of Aβ42 compared to solvent control. Strikingly, Aβ40 did not induce this effect (FIG. 4D). In addition, we stimulated splenocytes with LPS and treated with Aβ42, Aβ40, and solvent and assessed cell viability of CD11b+ macrophages and CD11c+ dendritic cells by FACS. We found that Aβ42 increased cell death in both macrophage and dendritic cell populations whereas Aβ40 did not (FIG. 10). Thus, our in vitro experiments demonstrate that Aβ42 induces cell death of activated lymphocytes and myeloid cells.

Figures 11, 12:
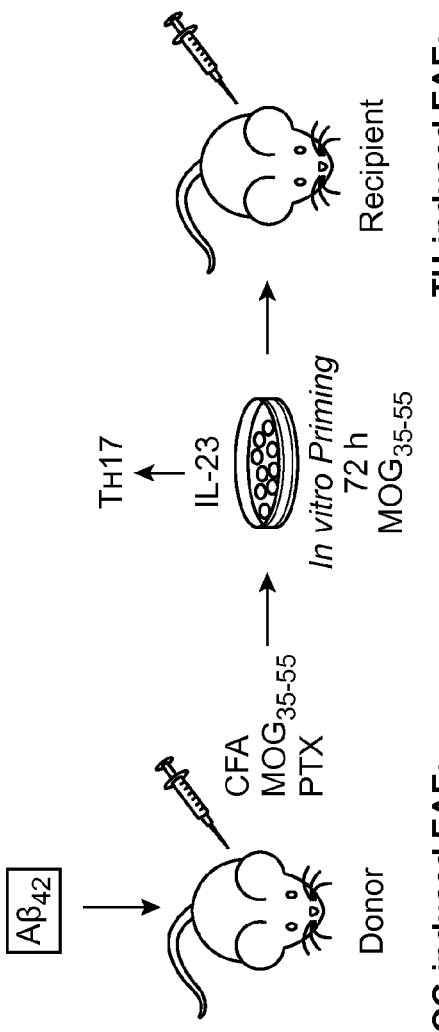
FIG. 11. Aβ treatment during EAE does not induce lymphopenia, thrombocytopenia or anemia. (a) Values are mean±s.d. values. (b) Treatment denotes in vivo administration of Aβ42, Aβ40 or solvent control initiated two days prior to EAE-immunization and continuing three times per week (300 ug ml-1) in prevention model. Sera extracted 10 days post EAE induction (n=3 mice per treatment group).
FIG. 12. Schematic of experimental paradigm demonstrating the effect of Aβ42 on the immune system is sufficient to ameliorate EAE.

These results led us to examine whether treatment with Aβ42 selectively targets activated immune cells or whether administration of this cytotoxic peptide induces lymphopenia, anemia, or thrombocytopenia in EAE mice. We analyzed complete blood counts of Aβ42- and Aβ40-treated EAE mice 10 days after immunization in the prevention model. Assessment of platelet, white blood cell, and red blood cell populations revealed that neither Aβ42-nor Aβ40-treatment in vivo made mice anemic, lymphopenic, or thrombocytopenic (FIG. 11). These data reinforce the concept that Aβ selectively suppresses activated lymphocytes and does not induce global lymphopenia in vivo.

Because Aβ42 induces death of lymphocyte and myeloid populations, we wanted to directly examine whether the effect of Aβ42 on the peripheral immune compartment, rather than the neuronal compartment, is sufficient to ameliorate EAE. We therefore induced EAE in WT mice and treated donor mice with Aβ42 three times a week for 10 days (FIG. 12). We then collected spleen and lymph node cells and re-stimulated in Th17-priming conditions with the MOG antigen ex vivo. The same number of viable cells, as confirmed by Trypan Blue staining, were injected i.p. into naïve recipient mice to induce Th17 EAE. Of note, recipient mice were not treated with any Aβ peptides. In recipient mice injected with Aβ42-treated immune cells, EAE severity decreased significantly (FIG. 4E). Thus indicating that the immunosuppressive effect of Aβ42 on the peripheral immune compartment in vivo is sufficient to ameliorate EAE and that Aβ42-treated immune cells, while still capable of causing EAE in recipient mice, were not as encephalitogenic compared to solvent control-treated immune cells.

Figures 13, 14:
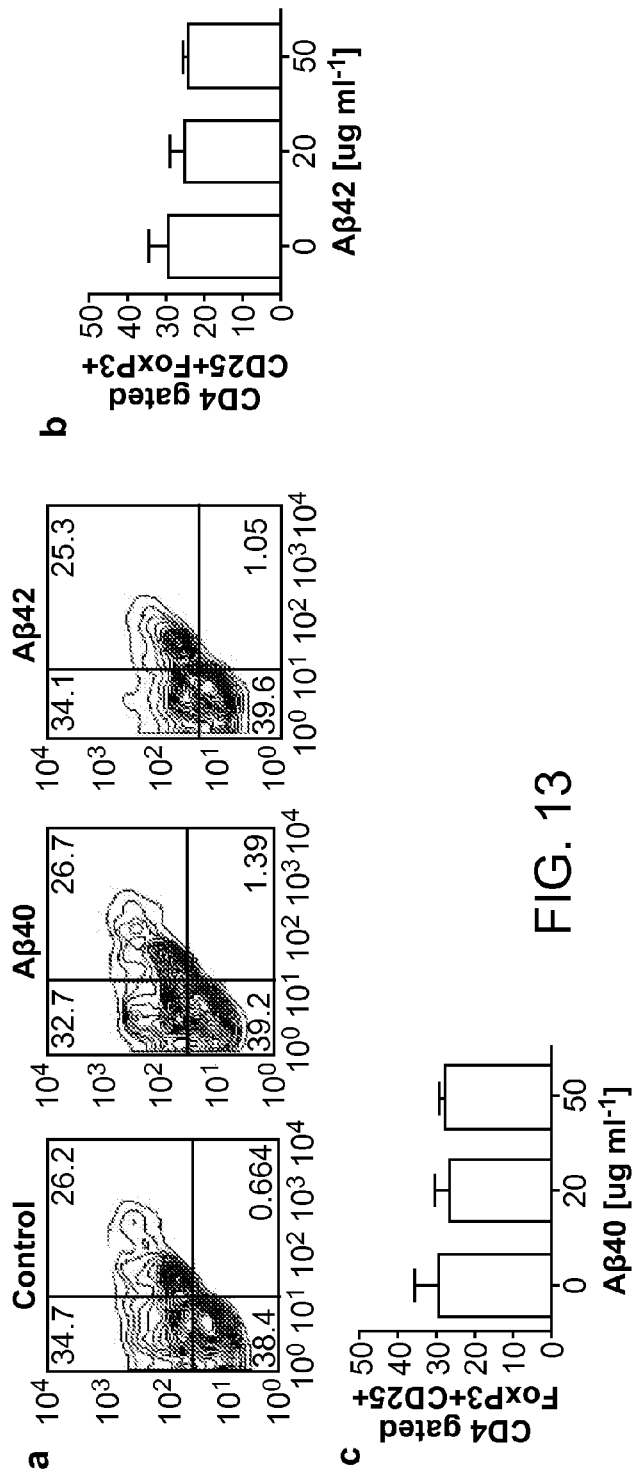
FIG. 13. Aβ peptides do not affect differentiation of inducible FoxP3+ Tregs. (a-c) CD8-depleted splenocytes stimulated with Aβ42 (b) or Aβ40 (c) in Treg-favoring conditions (IL-2, TGFβ, αCD3). Contour plots (a) and quantification (b,c) of frequency of CD25+FoxP3+ cells gated on CD4+ cells as assessed by FACS. Results representative of three experiments of n=2 or n=3 mice per treatment group. Splenocytes stimulated for 48 or 72 h. Error bars show s.e.m.
FIG. 14. Adoptive transfer EAE in WT and APP−/− mice. (A) Data shown as mean±s.e.m. values. (b) WT or APP−/− mice were adoptively transferred with MOG-sensitized encephalitogenic T lymphocytes from MOG-immunized C57BL/6 donor mice. (c) Numbers in parenthesis are the number of total animals per recipient group tested. (*P<0.05) (*P<0.02).
Figure 15:
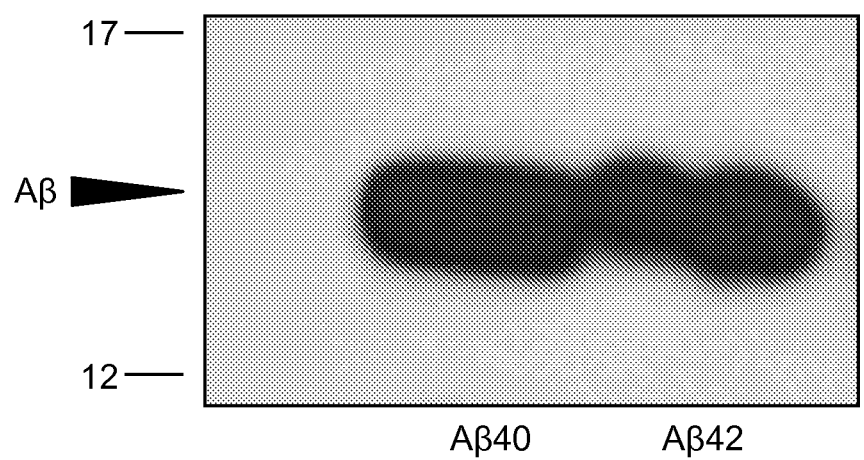
FIG. 15. Western blot. 2 µg of synthetic Aβ40 or Aβ42 peptide were loaded onto a Mini-Protean TGX Precast Gel 10% (BioRad) and subjected to SDS-PAGE electrophoresis. Proteins were transferred to a PVDF membrane (Immobilon Transfer Membrane, Millipore), immunoblotted with 6E10 antibody (Covance), and visualized by enhanced chemiluminescence (ECL Plus Western Blotting Detection System, GE Healthcare). Representative of three western blot experiments.

Next, we investigated the possibility that Aβ peptides protect against autoimmunity by inducing the expansion of a FoxP3+ regulatory T-cell (Treg) population. Tregs have been implicated in suppressing autoimmunity and maintaining immune homeostasis during inflammation and disease. Therefore, we examined the effect of Aβ42 and Aβ40 on CD4+FoxP3+ T-cells stimulated in vitro with IL-2, TGF-β, αCD3 antibodies and APCs. Neither Aβ42 nor Aβ40 significantly altered the frequency of CD4+CD25+FoxP3+ cells, as assessed by FACS (FIG. 13). Type 1 regulatory T (Tr1) cells, a subset that can differentiate independently of FoxP3, are the major IL-10-producing Treg subset. Such cells can confer protection through secretion of IL-10, an anti-inflammatory cytokine that has been associated with remission from EAE. Aβ42 and Aβ40 treatment of splenic cells cultured in Treg-priming conditions led to decreased production of the regulatory cytokine IL-10, measured by ELISA. Of note, IL-4 secretion, a Th2 cytokine, was undetectable. Taken together, these results imply that Aβ protection was not due to increased Foxp3+ Treg differentiation nor due to augmented IL-10 secretion from Tr1 cells.

Aβ42-mediated cell death is a phenomenon that is remarkably absent with Aβ40 treatment. Thus we speculated that Aβ40 and Aβ42 treatment could alter the cytokine signaling networks, perhaps in different manners, during EAE and could account for its therapeutic effect. We therefore used a multiplex bead system, Luminex, to measure the serum concentrations of 24 cytokines and chemokines in Aβ42- and Aβ40-treated EAE mice (FIG. 4F). Congruent with EAE protection, the majority of cytokines examined were mutually downregulated by both Aβ treatments during EAE. However, cluster analysis of cytokine profiles of Aβ42- and Aβ40-treated mice, normalized against control EAE mice, revealed a unique cytokine signature that differentiated between the two Aβ treatments. Eotaxin, G-CSF (granulocyte colony-stimulating factor), IFN-γ, and IL-12p40 were prominently downregulated in Aβ40-treatment and upregulated in Aβ42-treatment.

Thus far, we have shown that exogenous Aβ treatment protects against autoimmune-mediated damage against the CNS in four different models of EAE. Aβ treatment in the periphery is in accordance with the fact that Aβ peptides do endogenously exist in the peripheral blood system. To further solidify the 'gain of function' experiments in which exogenous Aβ42 and Aβ40 protect against EAE, we conducted the 'loss of function' experiment using mice lacking ubiquitous expression of APP, the precursor protein that yields both Aβ42 and Aβ40 (APP−/−). Administration of encephalitogenic T-cells sensitized to MOG induces more severe EAE in APP−/− mice than in WT mice (FIG. 4G). Interestingly, adoptive transfer EAE produces an intense immune conflagration in APP−/− mice leading to atypical EAE characterized by anaphylaxis and hunched, huddled posturing in addition to classical EAE symptoms (FIG. 14). Therefore, in the absence of APP, EAE disease progression is worse, consistent with our findings that administration of exogenous Aβ peptides ameliorates EAE.

Here we show that Aβ42 and Aβ40, thought to be culprits in the pathology of Alzheimer's disease, have unforeseen beneficial effects in autoimmune-mediated demyelination. Aβ treatment suppressed activated lymphocytes, which are capable of penetrating the CNS, thereby providing a protective effect in four major models of EAE, representing chronic progressive disease (C57BL/6), relapsing remitting disease (SJL/J), adoptive Th1 transfer, and adoptive Th17 transfer. Yet Aβ42 and Aβ40 afford protection by different mechanisms.

The difference in two amino acid residues between Aβ42 and Aβ40 provides different molecular properties, as Aβ42 is hydrophobic, relatively insoluble, and more amyloidogenic compared to Aβ40. Characterization of the biochemical and biophysical nature of the Aβ42 and Aβ40 peptides by western blot analysis has confirmed that the experimental peptides are enriched for monomeric and oligomeric fractions. Both molecules are able to attenuate inflammation and improve clinical status in the quintessential model of CNS autoimmunity, EAE. The Aβ peptides were administered in the periphery, and are likely to modulate the pathogenic potential of inflammatory immune cells outside of the CNS. Modulating the dynamic efflux of Aβ deposition between the CNS and plasma provides beneficial outcomes in AD and also has an influence on autoimmune disease, as we show here.

The cytotoxicity of Aβ42 on lymphocytes is similar to what is observed in mechanistic studies in AD, where Aβ42 is a potent mediator of neuronal cell death. The present experiments demonstrating the toxicity of Aβ42 on peripheral immune cells might help explain the cytopathology of AD, which is generally devoid of lymphocytes and macrophages entering from outside the CNS. Lymphoid populations that might normally home to regions with TNF, IL-1, and complement, are strikingly absent in AD, and this may be a consequence of the intense deposits of Aβ in AD plaques. Aβ is not as highly concentrated in MS lesions as it is in AD plaques. Thus, TNF, IL-1 and complement all act in MS to trigger an influx of immune cells from the periphery. The importance of this influx of immune cells from the periphery is emphasized in a potent approved therapy for MS, where blockade of this entry of immune cells to the CNS with an antibody to α4 integrin is highly beneficial in reducing relapses and ameliorating disability.

These results suggest that the role of Aβ might be dependent on the inflammatory context; specifically whether the cellular targets and source of inflammation originate in secondary lymphoid tissues or the glial-rich microenvironment of the brain. Experimental context concerning the preparation of Aβ is also important when considering the fact that AD patients immunized with Aβ develop a type of encephalomyelitis, likely due to the fact that the Aβ used in the vaccine AN-1792 was formulated in an adjuvant in order to purposely make it immunogenic. In our experiments, Aβ is given without adjuvant and it is remarkably immune suppressive. Aβ may have diverse Janus-like roles that are pathological or beneficial, in response to various injuries to the CNS. These findings provide new strategies for treating MS and related disorders of CNS autoimmunity with Aβ peptides administered in the periphery.

Methods Summary

EAE induction. In the C57BL/6 model, EAE was induced in 8- to 12-week old female mice by subcutaneous immunization with 100 μg $MOG_{35-55}$ in emulsified Complete Freund's Adjuvant (CFA) followed by intraperitoneal injection of 500 ng of Bordetella pertussis toxin (Difo Laboratories) in PBS at the time of, and two days following immunization. In the SJL/J EAE model, EAE was induced in 8- to 12-week old SJL/J female mice by subcutaneous injection with 100 μg $PLP_{139-151}$ peptide in emulsified CFA.

The classical clinical manifestation of EAE is ascending motor paralysis, starting in the tail and leading to forelimb paralysis.

For T helper ($T_H$)-induced EAE in the C57BL/6 strain, on day 10, after induction of EAE as described above, we re-stimulated splenic and axillary lymph node cells with $MOG_{35-55}$ peptide and 10 ng $ml^{-1}$ of IL-23 (Th17) (R & D Systems) for 3 days and transferred $5 \times 10^7$ cells into healthy recipients. In $T_H$-induced EAE, recipient mice present atypical EAE symptoms that are characterized by defects in rotatory movement and ataxia with little hind limb paralysis, as well as classical clinical symptoms.

In Vitro Mouse Immune Cell Activation Assays, Cytokine Analysis, and Differentiation.

We isolated splenic cells from C57BL/6 naïve mice and cultured at a density of $2 \times 10^5$ splenic cells in triplicate with antibodies to CD3 and CD28 at a concentration of 300 or 1000 (ng $ml^{-1}$) in the presence of Aβ42 or Aβ40 peptides (20 μg $ml^{-1}$ and 50 μg $ml^{-1}$) or DMSO/PBS solvent control. Culture plates were harvested at different time points (48, 72, or 96 h). We measured cytokine secretion by sandwich enzyme-linked immunosorbent assay (ELISA)(BD Pharmigen) and proliferation by radioactive [$^3$H]-thymidine incorporation. Cells were pulsed at 16 h prior to thymidine detection.

For Treg differentiation, we mechanically disrupted whole spleens to obtain cell suspension and depleted CD8+ T-cells by magnetic microbead selection (Miltenyi). We then stimulated cells for 3 d with αCD3 beads (1 μg $ml^{-1}$) (Ebioscience) in Treg polarizing (10 ng $ml^{-1}$ TGF-β, 10 ng $ml^{-1}$ IL-2)(R&D Systems) conditions in the presence of Aβ42 or Aβ40 peptides (20 μg $ml^{-1}$ and 50 μg $ml^{-1}$) or DMSO/PBS solvent control. Frequency of CD4 gated CD25+FoxP3+ Treg splenic cells was assessed by flow cytometry. IL-10 cytokine secretion was detected by ELISA from cell supernatant 72 h after stimulation.

Mouse lymphoid and myeloid cell viability assays. We cultured splenocytes from C57BL/6 naïve mice for 48 h or 72 h in stimulating medium either with αCD3, αCD28 (1 μg $ml^{-1}$) for T-cell stimulation or LPS (1 μg $ml^{-1}$)(Sigma) for antigen-presenting cell (APC) stimulation. We assessed the frequency of viable cells by FACS in cell cultures treated with Aβ42 or Aβ40 peptides (20 or 50 ug $ml^{-1}$) or DMSO/PBS solvent control using DiOC6, a fluorescent lipophilic dye that selectively targets intact mitochondrial membrane, distinguishing viable ($DiOC6^{high}$-expressing) from nonviable ($DiOC6^{low}$-expressing) cells. We assessed the frequency of viable splenic CD4+ T-cells or CD11c+ dendritic cells using fluorescent cell surface markers by flow cytometry.

Aβ. A peptide of amino acids 1-42 of human β-Amyloid and a peptide of amino acids 1-40 of human β-Amyloid were synthesized by the Stanford School of Medicine Protein and Nucleic Acid Facility (PAN Facility) on a ABI 433A peptide synthesizer with UV monitoring using standard Fmoc chemistry. Amino acid sequences of Aβ42 (SEQ ID NO:1 DAEFRHDSGYEVHHQKLVFFAEDVGSNKGAIIGLMVG-GVVIA) and Aβ40 (SEQ ID NO:2 DAEFRHDSGYEVHHQKLVFFAEDVGSNKGAIIGLM-VGGVV). All peptides synthesized were analyzed and purified by reverse phase HPLC on a C18 column and their molecular weight confirmed by Mass Spectrometry using a MALDI-TOF Voyager DE-RP instrument. In brief, solid peptides were diluted in DMSO at 30 mg $ml^{-1}$ and incubated at 37° C. overnight prior to PBS dilution and in vivo or in vitro administration.

What is claimed is:

1. A method for treating n multiple sclerosis in a patient, the method comprising:
   administering systemically to contact peripheral blood lymphocytes in said patient a therapeutically effective dose of an amyloid beta peptide selected from the group consisting of Aβ40 and Aβ42 in the absence of adjuvant, wherein immune cells in tissues affected by multiple sclerosis have decreased activation in the presence of the amyloid beta peptide.

2. A method for treating multiple sclerosis in a patient, the method comprising:
   administering systemically to contact peripheral blood lymphocytes in said patient a therapeutically effective dose of a biologically active peptide comprising at least 20 amino acids of Aβ40 or Aβ42 in the absence of adjuvant, wherein immune cells in tissues affected by multiple sclerosis have decreased activation in the presence of the peptide.

3. The method of claim 1, wherein the agent is administered in a combination therapy with a second antigen-specific or non-antigen specific agent.

* * * * *

SEQUENCE LISTING

<160> NUMBER OF SEQ ID NOS: 2

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40